US011278501B2

(12) United States Patent
Beach-Herrera et al.

(10) Patent No.: US 11,278,501 B2
(45) Date of Patent: Mar. 22, 2022

(54) METHOD AND SYSTEM FOR FORMING A DOSAGE FORM WITHIN A PACKAGING

(71) Applicant: APRECIA PHARMACEUTICALS LLC, Blue Ash, OH (US)

(72) Inventors: Lauren E. Beach-Herrera, East Brunswick, NJ (US); Matthew F. Boldt, Santa Fe, NM (US); Thomas J. Bradbury, Yardley, PA (US); Henry Cabral, Hillsborough, NJ (US); Kelly E. Caputo, Langhorne, PA (US); William R. Gross, Lambertville, NJ (US); Munhee Lee, Princeton, NJ (US); Mahendra R. Patel, Delray Beach, FL (US); Aleece M. Phillips, Yardley, PA (US); Timothy S. Tracy, Huntsville, AL (US); Thomas G. West, Lawrenceville, NJ (US); Jaedeok Yoo, Princeton, NJ (US)

(73) Assignee: APRECIA PHARMACEUTICALS LLC, Blue Ash, OH (US)

( * ) Notice: Subject to any disclaimer, the term of this patent is extended or adjusted under 35 U.S.C. 154(b) by 0 days.

(21) Appl. No.: 17/285,186

(22) PCT Filed: Oct. 15, 2019

(86) PCT No.: PCT/US2019/056323
§ 371 (c)(1),
(2) Date: Apr. 14, 2021

(87) PCT Pub. No.: WO2020/081561
PCT Pub. Date: Apr. 23, 2020

(65) Prior Publication Data
US 2021/0393533 A1 Dec. 23, 2021

Related U.S. Application Data

(60) Provisional application No. 62/745,750, filed on Oct. 15, 2018.

(51) Int. Cl.
*A61J 3/06* (2006.01)
*A61K 9/00* (2006.01)
(Continued)

(52) U.S. Cl.
CPC .............. *A61K 9/2095* (2013.01); *A61J 1/035* (2013.01); *A61J 3/06* (2013.01); *A61K 9/0056* (2013.01)

(58) Field of Classification Search
CPC ........... A61J 1/035; A61J 3/06; A61K 9/0056; A61K 9/2095
See application file for complete search history.

(56) References Cited

U.S. PATENT DOCUMENTS

| 4,305,502 A | 12/1981 | Gregory et al. |
|---|---|---|
| 4,631,837 A | 12/1986 | Magoon |

(Continued)

FOREIGN PATENT DOCUMENTS

| CN | 104760767 | 7/2015 |
|---|---|---|
| JP | H07-508676 | 9/1995 |

(Continued)

OTHER PUBLICATIONS

Alhnan et al. (Pharm Res. 2016;33:1817-1832) (Year: 2016).*

(Continued)

*Primary Examiner* — Ernst V Arnold
(74) *Attorney, Agent, or Firm* — Daniel F. Nesbitt; Hasse & Nesbitt LLC

(57) ABSTRACT

A method and system of forming a pharmaceutical dosage form within a portion of a blister packaging. The method includes the steps of providing a blister packaging for the dosage form with depressions. A predetermined amount of a drug-containing powder material comprising drug-containing particles is deposited into a substantially uniform powder layer within the depressions. A binding liquid is then (Continued)

deposited in a pattern on the powder layer within the depressions, to bind the particles of the powder layer and form an incremental wetted layer. Excess solvent in the binding material can be removed to form an incremental bound layer. These steps are repeated in sequence at least one or more times to form the pharmaceutical dosage form within the blister packaging.

20 Claims, 16 Drawing Sheets

(51) Int. Cl.
*A61K 9/20* (2006.01)
*A61J 1/03* (2006.01)

(56) References Cited

U.S. PATENT DOCUMENTS

| | | | |
|---|---|---|---|
| 5,343,672 | A | 9/1994 | Kearney et al. |
| 6,047,484 | A | 4/2000 | Bolland et al. |
| 6,471,992 | B1 | 10/2002 | Yoo et al. |
| 6,945,638 | B2 | 9/2005 | Teung et al. |
| 6,990,748 | B2 | 1/2006 | Magoon et al. |
| 7,300,668 | B2 | 11/2007 | Pryce Lewis et al. |
| 7,875,290 | B2 | 1/2011 | Payumo et al. |
| 8,088,415 | B2 | 1/2012 | Wang et al. |
| 8,516,714 | B2 | 8/2013 | Biemans et al. |
| 8,802,145 | B2 | 8/2014 | Bauer |
| 9,096,335 | B2 | 8/2015 | Ahuja et al. |
| 9,314,429 | B2 | 4/2016 | Jacob et al. |
| 9,339,489 | B2 | 5/2016 | Jacob et al. |
| 9,409,699 | B2 | 8/2016 | Weigel |
| 9,427,399 | B2 | 8/2016 | Adams et al. |
| 9,492,380 | B2 | 11/2016 | Jacob et al. |
| 9,828,119 | B2 | 11/2017 | Wolf |
| 9,833,955 | B2 | 12/2017 | Muller et al. |
| 10,071,372 | B2 | 9/2018 | Nitsch |
| 10,421,265 | B2 | 9/2019 | Houben et al. |
| 2003/0228368 | A1 | 12/2003 | Wynn et al. |
| 2008/0073372 | A1 | 3/2008 | Keller |
| 2009/0060983 | A1 | 3/2009 | Bunick et al. |
| 2010/0016348 | A1 | 1/2010 | Bunick et al. |
| 2010/0316712 | A1 | 12/2010 | Nangia et al. |
| 2014/0065194 | A1 | 3/2014 | Yoo et al. |
| 2014/0271862 | A1 | 9/2014 | Jacob et al. |
| 2016/0082658 | A1 | 3/2016 | Swartz et al. |
| 2017/0188616 | A1 | 7/2017 | Alfiere et al. |
| 2017/0312179 | A1 | 11/2017 | Gamberini |
| 2017/0322068 | A1 | 11/2017 | Gueller et al. |
| 2018/0031410 | A1 | 2/2018 | Lux et al. |
| 2018/0141275 | A1 | 5/2018 | Patel et al. |
| 2019/0142743 | A1 | 5/2019 | Fuisz et al. |

FOREIGN PATENT DOCUMENTS

| | | |
|---|---|---|
| WO | 9412142 | 6/1994 |
| WO | 0328990 | 4/2003 |
| WO | 2014039378 | 3/2014 |
| WO | 2015159300 | 10/2015 |
| WO | 2017034951 | 3/2017 |

OTHER PUBLICATIONS

International Search Report with Written Opinion dated Oct. 6, 2021 by the International Searching Authority for related International Application No. PCT/US2021/027558, filed Apr. 15, 2021 (15 pages).

Norman, et al., "A new chapter in pharmaceutical manufacturing: 3D-printed drug products.", www.sclencedirect.com/science/article/abs/pii/s0169409x16300771, Advanced Drug Delivery Reviews 108 (Jan. 1, 2017): 39-50, Abstract (1 page).

"Vibrating Tables", Tinsley Equipment Company, Apr. 3, 2012, https://www.tinsleycompany.com/bulk-process-equipment/vibratory-process-equipment/vibrating-tables/ (6 pages).

"Flex PowderDose", ChemSpeed Technologies Inc., Aug. 17, 2017, https://www.chemspeed.com/flexpowderdose/ (5 pages).

Jamroz et al., "3D Printing in Pharmaceutical and Medical Applications—Recent Achievements and Challenges", Pharm Res, vol. 35, No. 176, Jul. 11, 2018 (22 pages).

"Solid surface energy data (SFE) for common polymers", Surface-tension.de, Dec. 5, 2004, http://www.surface-tension.de/solid-surface-energy.htm (2 pages).

International Search Report and Written Opinion dated Jan. 23, 2020 by the European Patent Office (as International Search Authority) for corresponding International Application No. PCT/US2019/056323 filed Oct. 15, 2019 (13 pages).

Supplemental International Search Report and Written Opinion by the USPTO, publicly available Apr. 23, 2020, for corresponding International Application No. PCT/US2019/056323 filed Oct. 15, 2019 (7 pages).

Supplemental International Search Report and Written Opinion by the KIPO, publicly available Apr. 23, 2020, for corresponding International Application No. PCT/US2019/056323 filed Oct. 15, 2019 (20 pages).

Supplemental International Search Report and Written Opinion by the CNIPA, publicly available Apr. 23, 2020, for corresponding International Application No. PCT/US2019/056323 filed Oct. 15, 2019 (10 pages).

Supplemental International Search Report and Written Opinion by the JPO, publicly available Apr. 23, 2020, for corresponding International Application No. PCT/US2019/056323 filed Oct. 15, 2019 (8 pages).

Written Opinion of the IPEA dated Sep. 4, 2020 by the European Patent Office, for corresponding International Application No. PCT/US2019/056323 filed Oct. 15, 2019 (8 pages).

International Preliminary Report on Patentability (Chapter II) dated Jan. 20, 2021 by the European Patent Office (IPEA), for corresponding International Application No. PCT/US2019/056323 filed Oct. 15, 2019 (8 pages) with Annex of amended claims (10 pages).

* cited by examiner

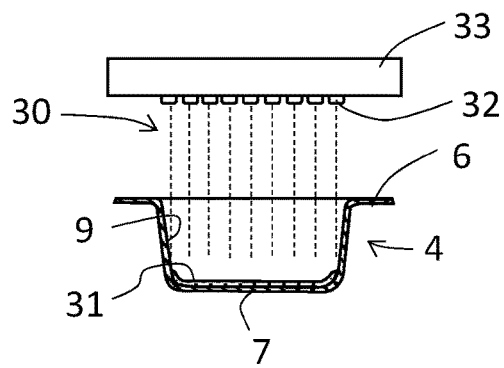
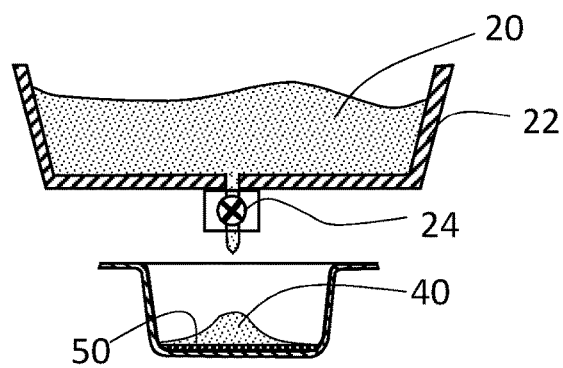
Fig. 5
Fig. 6
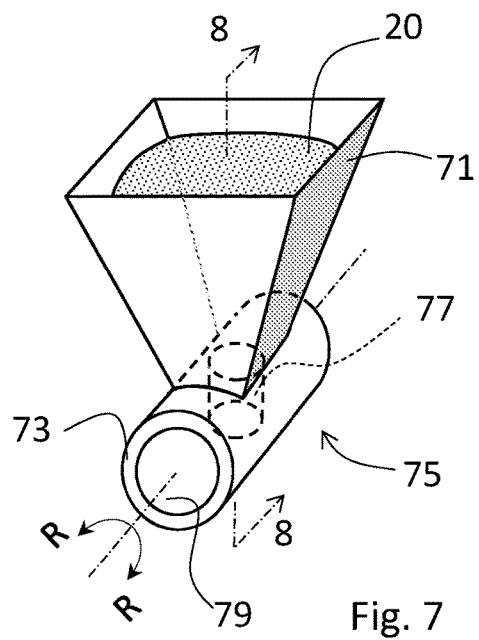
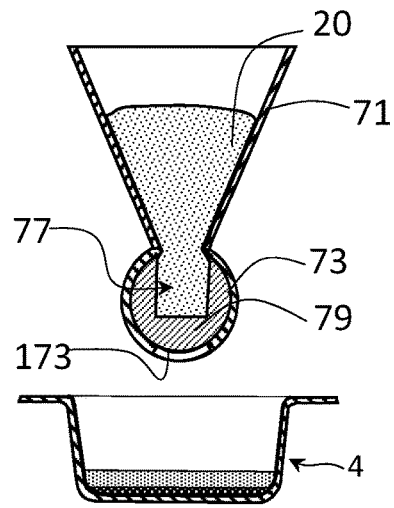
Fig. 7
Fig. 8
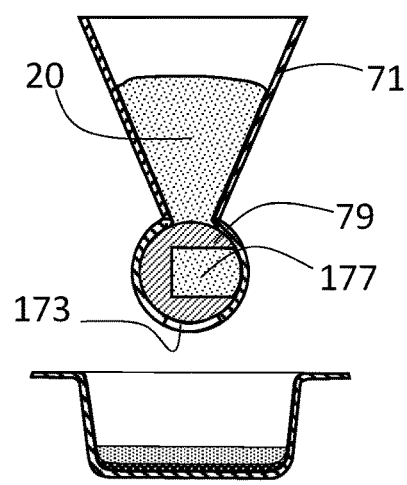
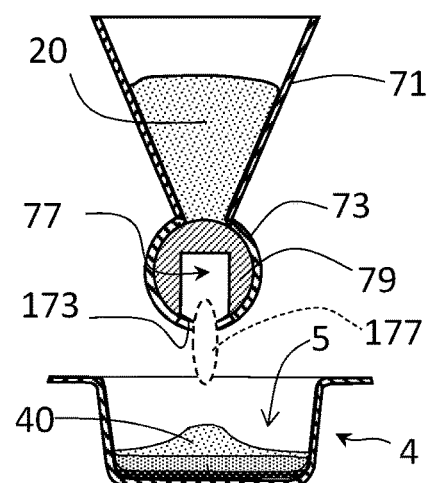
Fig. 9
Fig. 10

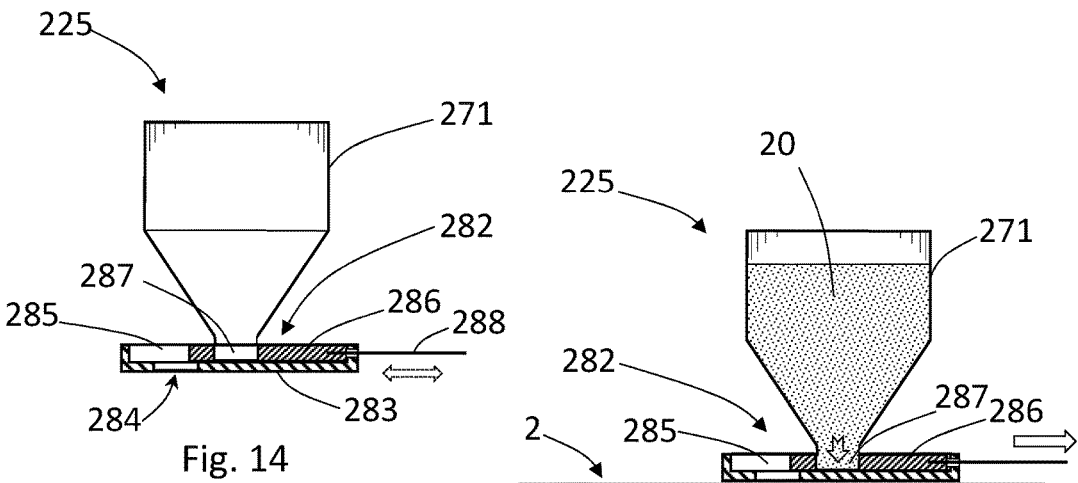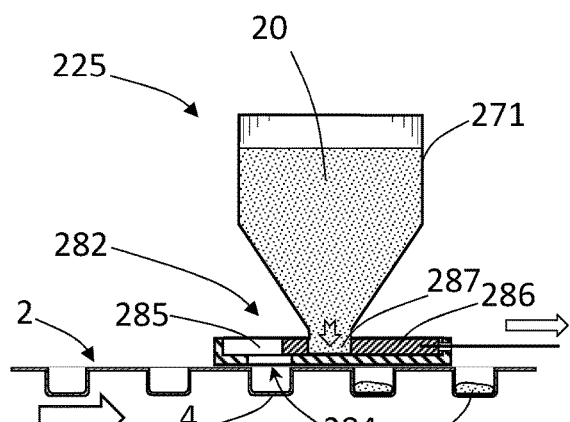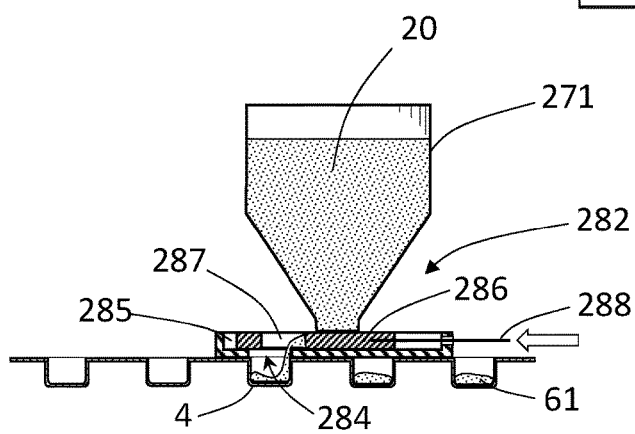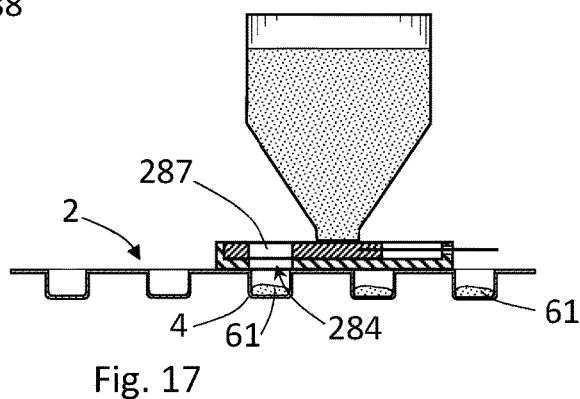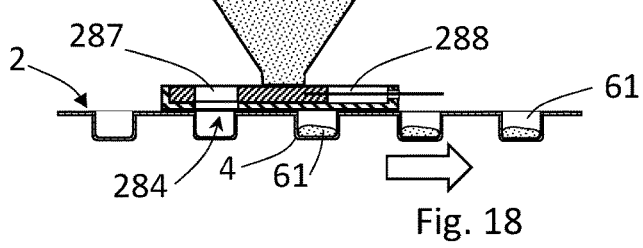

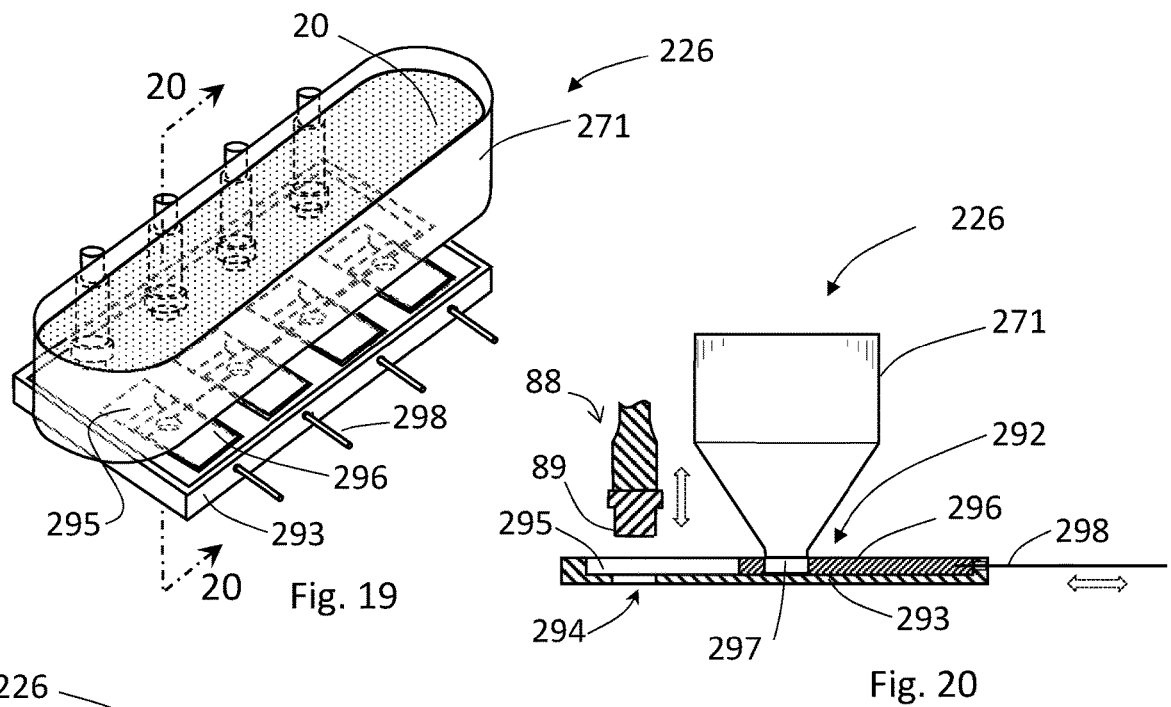
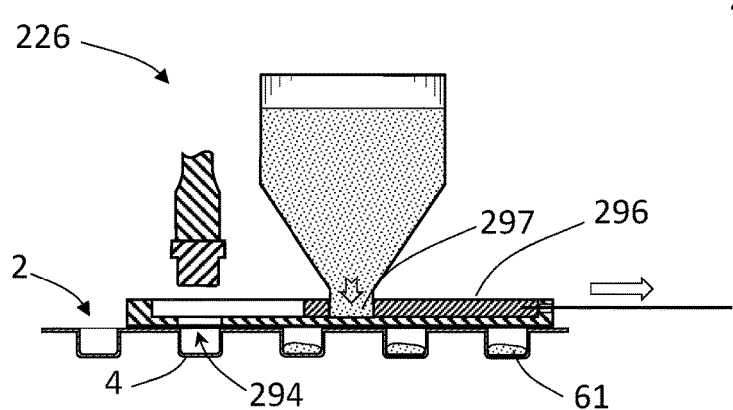
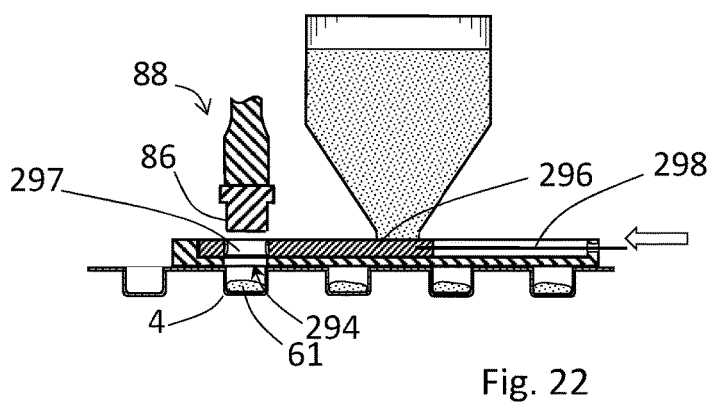

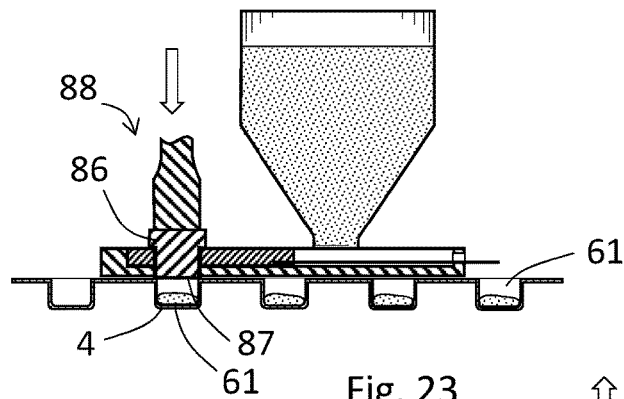
Fig. 23
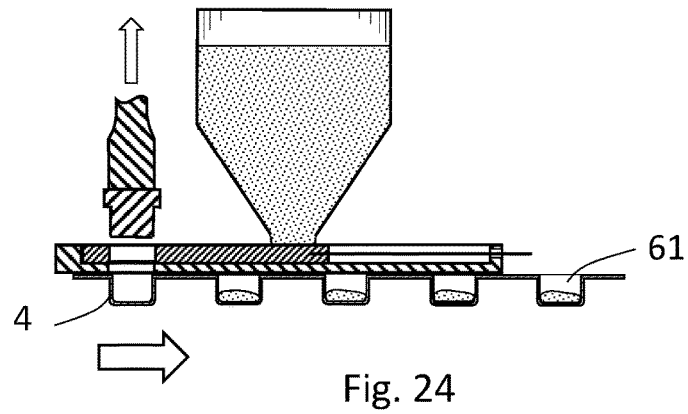
Fig. 24
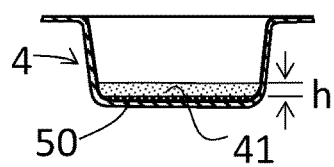
Fig. 25
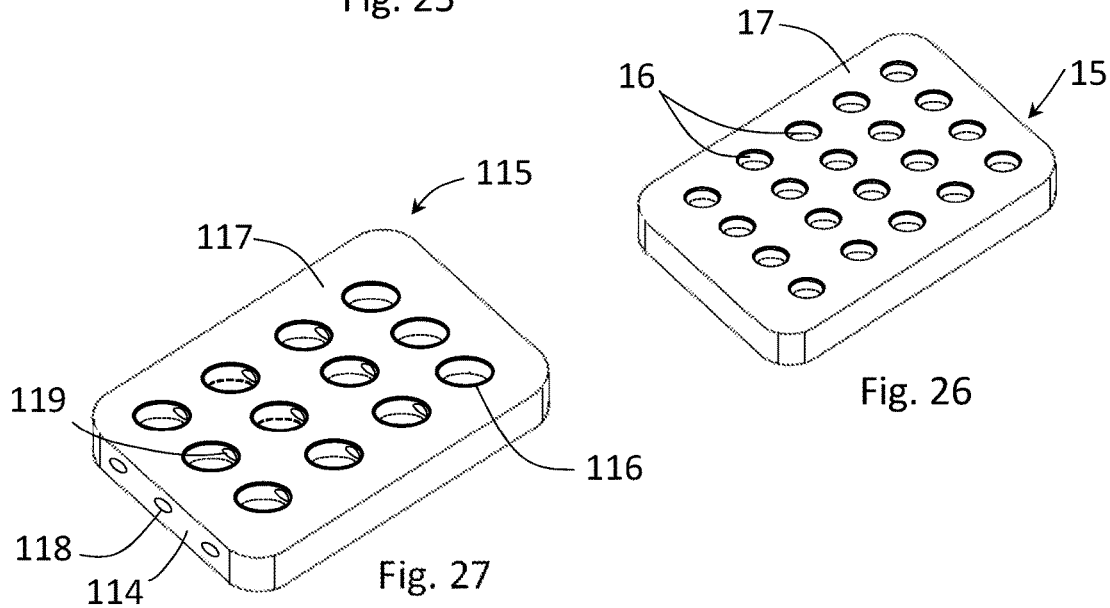
Fig. 26
Fig. 27

METHOD AND SYSTEM FOR FORMING A DOSAGE FORM WITHIN A PACKAGING

CROSS-REFERENCE TO RELATED APPLICATIONS

The present application is a National Stage Entry of International Application Number PCT/US2019/056323, filed Oct. 15, 2019, which claims the benefit of U.S. Provisional Application Ser. No. 62/745,750, filed Oct. 15, 2018, the disclosures of which are hereby incorporated by reference in their entireties.

FIELD OF THE INVENTION

This invention relates to the field of manufacturing of dosage or tablet forms for pharmaceuticals or other active ingredients.

BACKGROUND OF THE INVENTION

In recent years, pharmaceutical producers have turned to the use of blister packs for use in both the forming and dispensing of pharmaceutical tablets. These blister packs generally consist of a blister sheet or blister film and a lidding sheet. The blister sheet contains spatial depressions for containing individual dosages, including tablets, capsule, pills, etc.

In a standard process for manufacturing freeze-dried tablets, a single dosage, in liquid form, is introduced into each depression of the blister sheet. The blister sheet, along with the liquid dosages, is then placed into a refrigerated environment where the dosages are subjected to low temperatures to freeze them. The blister sheets are then transferred to a freeze drier, where the ice is removed by sublimation. When freeze drying is completed, the sheets are removed from the drying chamber and covered with an adhesive lidding sheet, which seals the solid dosages into their individual depressions. International Publication WO/1994/012142 is incorporated herein by reference as teaching, inter alia, known processes for manufacturing freeze dried tablets in a blister package.

Notwithstanding, a freeze-drying or lyophilizing method may have significant, negative impacts on product activity, shelf stability, and batch consistency and repeatability. The process inherently is expensive in terms of energy and manpower resources, and quality control and regulatory requirements present additional challenges. In some cases, the freeze-drying or lyophilizing method is simply unsuitable for a particular drug or pharmaceutical.

Rapid prototyping describes various techniques for fabricating a three-dimensional prototype of an object from a computer model of the object. One technique is three-dimensional printing, whereby a printer is used to fabricate the 3-D prototype from a plurality of two-dimensional layers. In particular, a digital representation of a 3-D object is stored in a computer memory. Computer software sections the representation of the object into a plurality of distinct 2-D layers. Alternatively, a stream (sequential series) of instructions for each incremental layer may be entered directly, e.g. a series of images. A 3-D printer then fabricates a thin layer of bound material for each 2-D image layer sectioned by the software. Together, the layers are printed one on top of the other and adhere to each other to form the desired prototype.

Powder-liquid three-dimensional printing technology has been used to prepare articles such as pharmaceutical dosage forms, mechanical prototypes and concept models, molds for casting mechanical parts, bone growth promoting implants, electronic circuit boards, scaffolds for tissue engineering, responsive biomedical composites, tissue growth promoting implants, dental restorations, jewelry, fluid filters and other such articles.

Three-dimensional printing can include a solid freeform fabrication technique/rapid-prototyping technique in which thin layers of powder are spread onto a surface and selected region of the powder are bound together by the controlled deposition ("printing") of a liquid. This basic operation is repeated layer-by-layer, with each new layer formed on top of and adhered to the previously printed layer, to eventually make three-dimensional objects within a bed of unbound powder. When the printed objects have sufficient cohesion, they may be separated from the unbound powder.

Systems and equipment assemblies for three-dimensional printing of articles are commercially available or in use by others, for example: Massachusetts Institute of Technology Three-Dimensional Printing Laboratory (Cambridge, Mass.), Z Corporation's (now part of 3D Systems) 3DP and HD3DP™ systems (Burlington, Mass.), The Ex One Company, L.L.C. (Irwin, Pa.), Soligen (Northridge, Calif.), Specific Surface Corporation (Franklin, Mass.), TDK Corporation (Chiba-ken, Japan), Therics L.L.C. (Akron, Ohio, now a part of Integra Lifesciences), Phoenix Analysis & Design Technologies (Tempe, Ariz.), Stratasys, Inc.'s Dimension™ system (Eden Prairie, Minn.), Objet Geometries (Billerica, Mass. or Rehovot, Israel), Xpress3D (Minneapolis, Minn.), and 3D Systems' Invision™ system (Valencia, Calif.).

Three-dimensional printing systems employing powder and binding liquid typically form articles by depositing binding liquid onto the individual, sequentially-applied layers of the powder. The binding liquid is applied in patterns to predetermined regions of the powder in each powder layer such that unbound powder material remains on the outer periphery of the patterns. The unbound powder typically surrounds the printed articles that are being formed. The printed articles, which comprise bound powder, are then separated from substantial amounts of unbound powder. Such processes undesirably require wasting or recycling the unbound powder. It would be a substantial improvement in the field to provide an equipment assembly, system and method for substantially reducing or eliminating the need to waste or recycle unbound powder.

US Patent Publication 2018/0141275, the disclosure of which is incorporated herein by reference, describes manufacturing systems, equipment assemblies, and use thereof for the preparation of articles by cavity three-dimensional printing. The cavities may be part of build modules on the machine within which articles are formed that approximate the periphery of the cavity. The articles are formed by a succession of plural incremental layers formed within the cavities. Following completion, a 3DP article is discharged from the cavity. The 3DP article is optionally dried, optionally dedusted, and/or optionally packaged.

A need therefore remains for improved and more convenient pharmaceutical dosage forms, and their method for making.

SUMMARY OF THE INVENTION

The present invention provides a method and system for the forming of a bound-powder or bound-particulate article within a volume of a depression of a packaging material, and for an article of manufacture that is formed in situ within the depression of its packaging. In some embodiments, the article is a dosage form, which can be a medicament, drug, or pharmaceutical tablet or pill, including solid oral prescription drugs. The methods described herein are also referred to as depression three-dimensional printing, or depression 3DP. The packaging can comprise one or more, and in some embodiments a pattern of a plurality of depressions. The method and system can be used for high throughput continuous, semi-continuous, or batch manufacture with minimal product loss, high efficiency, and high product reproducibility.

The embodiments and features described herein provide a method for the formation of pharmaceutical- and drug-containing tablets directly within their packaging, such as a blister pack, and in a particular embodiment, a method for making rapidly-disintegrating pharmaceutical tablets in disposable single-dose blister packs.

The embodiments described herein can provide a substantial reduction in or elimination of waste or recyclable unbound powder as compared to other three-dimensional printing (3DP) processes. Depression 3DP provides for most, substantially all, or all of the particulate material entering a depression to be incorporated into a corresponding single 3-D printed dosage form.

The embodiments described herein provide a method of forming a dosage form within a portion of a packaging for the dosage form. The method comprises the steps of: 1) providing a portion of a packaging for the dosage form, the portion of the packaging comprising at least one depression; 2) depositing a predetermined amount of a powder material comprising particles into a powder layer within the at least one depression; 3) depositing a binding liquid in a pattern on the powder layer within the at least one depression, to bind at least a portion of the particles of the powder layer to form an incremental bound layer; and 4) repeating steps 2) and 3) in sequence at least one or more times, thereby forming a dosage form within the portion of the packaging for the dosage form.

The embodiments described herein also provide a method of forming a dosage form within a portion of a packaging for the dosage form, comprising the steps of: 1) providing a portion of a packaging for the dosage form, comprising at least one spatial depression, 2) depositing a predetermined amount of a powder material comprising particles into a powder layer within the at least one depression, 3) depositing a binding liquid in a pattern on the powder layer within the at least one depression, to bind at least a portion of the particles of the powder layer to form an incremental wetted layer, and 4) repeating steps 2) and 3) in sequence at least one or more times, thereby forming the dosage form within the portion of the packaging for the dosage form.

In some embodiments, the deposited layer of powder is a substantially uniform powder layer.

In either or both of the above methods, the powder material can be deposited into the at least one depression in a powder depositing region (or system) of an apparatus or system assembly, and the powder material can be layered, or formed into an incremental layer of powder material, in the powder depositing region (or system), or in a dedicated powder leveling region (or system) of an apparatus or system assembly. The binding liquid can be applied to the incremental powder layer when the receptacle is in the binding liquid application region (or system) of an apparatus or system assembly. The shaping or tamping of a powder material or a wetted material layer can be completed in the powder depositing region (or system) or the powder leveling region (or system) of an apparatus or system assembly, or in a dedicated shaping region (or system) of an apparatus or system assembly.

The dosage form packaging comprising the one or more depressions, can be movable between any two or more of the above-mentioned regions (or systems) in any order. In some non-limited embodiments, the receptacle(s) moves: a) from the powder depositing region to the binding liquid application region, repeatedly and then optionally to the shaping region; b) from the powder layering region to the shaping region, and then to the binding liquid application region; c) from the powder layering region to the binding liquid application region then back to the powder layering region and then to the shaping region; or d) from the powder layering region to the leveling region, then to the binding liquid application region, then to a drying region. A discharge region can be placed after the powder layering region, the binding liquid application region, the shaping region, and/or the drying region.

The manufactured product package can comprise a film material having one or more depressions therein, the one or more depressions, containing a shaped, bound-powder dosage form, formed within the one or more depressions, and a peelable or removable covering sheet adhered to the film material, so as to enclose the dosage form within the one or more depressions.

In an embodiment, the dosage form is a bound-powder matrix is formed within the one or more depressions by binding a powder deposited within the one or more depressions with a binding liquid.

In an embodiment, a portion of the shaped, bound-powder matrix conforms to an inner surface of the one or more depressions.

An embodiment can also provide a package comprising a film material having one or more depressions therein, the one or more depressions containing a shaped, bound-powder matrix formed within the one or more depressions, and a peelable covering sheet adhered to the film material, so as to enclose the bound-powder matrix within the one or more depressions.

In an embodiment, the bound-powder matrix is formed within the one or more depressions by binding a powder deposited within the one or more depressions with a binding liquid. A portion of the shaped, bound-powder matrix can conform to an inner surface of the one or more depressions. A peripheral portion of the bound-powder matrix that confronts the inner surface of the one or more depressions can include an additional amount of a binding liquid.

In an embodiment, the bound-powder matrix comprises a 3D printed, rapidly-dispersible dosage, and can be formed within the one or more depressions by binding a powder deposited within the one or more depressions with a binding liquid.

In an embodiment, the bound-powder matrix comprises an active pharmaceutical ingredient (API).

In another embodiment, a peripheral portion of the bound-powder matrix that confronts the inner surface of the one or more depressions includes an additional amount of a binding liquid.

In an embodiment, the at least one depression has a fixed shape and volume, which does not change or vary under ordinary use and handling of the packaging.

In an embodiment, the packaging comprises one or more blisters, cups, pods, or other receptacles.

In an embodiment, the packaging is pre-formed and/or pre-cut ahead of the dosage-forming process.

In an embodiment, the packaging comprises a sheet including a plurality of the depressions formed into the sheet, and where the depression includes a sidewall that extends from the sheet to the closed end.

In an embodiment, the step 4) is repeated at least three times.

In an embodiment, a portion of the powder material comprises particles of a binder material, and the binding liquid binds the particles of the binder material.

In an embodiment, the method can include a step, preceding step 2), of depositing a binding liquid on at least the closed end of the depression.

In an embodiment, the at least one depression includes an inner surface that includes a release agent.

In an embodiment, the binding liquid comprises a volatile solvent, and the method can include a step of evaporatively removing a portion of the volatile solvent from the incremental bound layer.

In an embodiment, the sidewall has a depression depth, and each powder layer has a thickness of at least 5%, and up to about 100%, and in some embodiments, up to about 50%, of the depression depth.

In some embodiment, the number of powder layers that are deposited into a depression and formed into an incremental bound-powder layer can be one or a plurality of layers, including two or more layers, three or more layers, four or more layers, five or more layers, six or more layers, seven or more layers, or eight or more layers, and up to fifty or fewer layers, forty or fewer layers, thirty or fewer layers, twenty or fewer layers, eighteen or fewer layers, sixteen or fewer layers, fourteen or fewer layers, twelve or fewer layers, ten or fewer layers, eight or fewer layers, six or fewer layers, or four or fewer layers, in any combination.

An incremental powder layer can have a target or weight average thickness, of a predetermined thickness (vertical height). In some embodiments, the predetermined thickness can be varied from 0.005 to 0.015 inches, 0.008 to 0.012 inches, 0.009 to 0.011 inches, about 0.01 inches, 100-300 µm, 100-500 µm, about 200 µm, or about 250 µm. In some embodiments, the thickness of the incremental powder layers range from 100-400 microns, 150-300 microns, or 200-250 microns. In one embodiment, the powder layer thickness is 200 microns. In another embodiment, the powder layer thickness is 250 microns.

In some embodiments, the predetermined thickness is at least 0.05 inches, at least 0.008 inches, at least 0.010 inches, at least 0.012 inches, at least 0.014 inches, or at least 0.016 inches, and up to 0.020 inches, up to 0.018 inches, up to 0.016 inches, up to 0.014 inches, up to 0.012 inches, or up to 0.010 inches. As thicker incremental layers are used, an increasing amount of printing fluid is deposited on that layer to ensure adequate binding both within the plane of the layer and layer-to-layer. Conversely, for a thinner incremental layer, a lesser amount of printing fluid is deposited to obtain the same extent of binding. For a given amount of printing liquid deposited per layer, using a larger layer thickness will reduce (worsen) dosage form handleability and reduce (improve) dispersion time. If too thick of a layer is used for a given amount of fluid, laminar defects may form that cause the dosage form to easily fracture along the plane of the layers (delamination), or the dosage form itself may not have adequate strength to handle at all.

Dosage forms produced by a 3DP process described herein can ranged in diameter (of equivalent diameter of a non-circular area) from about 13-14 mm to about 20-25 mm, and in height (total thickness) from about 5-6 mm to about 8-10 mm.

In an embodiment, the pattern of the binding liquid deposited on the powder layer has a periphery that is disposed against or in contact with the sidewall of the packaging.

In an embodiment, the pattern of the binding liquid deposited on the powder layer has a shape selected from the group consisting of an annular ring and a circle.

In an embodiment, the method can include a step of applying a lidding layer over the dosage form and the at least one depression to form a sealed packaging for the dosage form.

In an embodiment, the binding liquid is deposited by inkjet printing to form the wetted or bound powder layer.

In an embodiment, the step 2) of depositing the predetermined amount of the powder material comprising particles into the substantially uniform powder layer within the at least one depression, comprises: 1) depositing a predetermined amount of a powder material comprising particles into the at least one depression, and 2) forming the deposited, predetermined amount of the powder material into a substantially uniform powder layer within the at least one depression.

In an embodiment, the step of forming includes shaping and/or tamping the deposited, predetermined amount of the powder material into the formed powder layer having an upper surface. In another embodiment, the step of forming includes tamping a last deposited, predetermined amount of the powder material into a last formed powder layer having an upper surface.

In an embodiment, the method includes a step, following a step of depositing a binding liquid in a pattern on the powder layer within the at least one depression, comprising a step of shaping and/or tamping the incremental wetted layer into a shaped or tamped wetted layer. The formed wetted layer has an upper surface that in one embodiment is flat or planar, and in another embodiment is convex or concave.

In an embodiment, the method includes a step, following the formation of a plurality of incremental wetted layers into a wetter structure comprising multiple wetted layers, comprising a step of shaping and/or tamping the multiple wetted layer into a shaped or tamped wetted structure.

In an embodiment, the step of shaping and/or tamping employs a stamp or tamper. In some embodiments, the stamp has a lower concave surface.

In an embodiment, the powder material can comprise one or more types of drug-containing particles.

The present invention can also provide a 3DP equipment system and assembly for providing and positioning a depression or a pattern of depressions, for example, associated with dosage form packaging, and for the forming of 3DP dosage forms within the depressions. The equipment system and assembly can comprise, without limitation, a powder depositing system, disposed in a powder depositing region, a powder leveling system, disposed in a powder leveling region, a binding liquid application system, disposed in a binding liquid application region, a shaping system, disposed in shaping region, and a drying system, disposed in drying region.

In some embodiments, the 3DP equipment assembly can comprise a control system comprising one or more computerized controllers, one or more computers, and one or more user interfaces for one or more computers. In some embodiments, one or more components of the equipment assembly are computer controlled. In some embodiments, one or more components of the 3DP build system are computer controlled. In some embodiments, the powder depositing system, the powder leveling system, the binding liquid application system, the shaping system, disposed in shaping region, and the drying system, are computer controlled.

In some embodiments, a 3DP equipment assembly can also comprise one or more harvesting systems, one or more liquid removal systems, one or more powder recovery systems, one or more article transfer systems, one or more inspection systems. The 3DP equipment assembly, apparatus or system can comprise some or all of the above systems. For example, in certain embodiments of a cavity 3DP equipment assembly, apparatus, or system, it is not necessary to have a harvesting system since substantially all of the powder material entering a depression is incorporated into a respective dosage form formed within the depression, with little or no excess powder for separation.

BRIEF DESCRIPTION OF THE FIGURES

FIG. 5 illustrates a binding liquid being deposited onto the closed end of a depression.

FIG. 6 illustrates depositing a pile of powder material from a powder source into the depression.

FIG. 7 illustrates an example of a dosing apparatus that can deliver a predetermined amount of powder material inside a depression of a blister-type packaging including, but not limited to, by a predetermined mass weight and by a predetermined volume.

FIG. 8 illustrates a cross-section view of the dosing apparatus of FIG. 7, positioned to deposit a predetermined amount of powder material onto a bound powder layer in the depression of a blister-type packaging.

FIG. 9 illustrates the dosing apparatus of FIG. 7 having a fill cavity containing the predetermined amount of powder material being isolated from the powder supply.

FIG. 10 illustrates the dosing apparatus of FIG. 7 wherein the predetermined amount of powder material is being deposited into the depression.

FIG. 14 shows an elevation sectional view through the automated dosing apparatus and volumetric dispensing pocket of FIG. 13.

FIG. 15 shows an elevation sectional view through the automated dosing apparatus and volumetric dispensing pocket of FIG. 14, with a powder bin and the fill pocket filled with powder material.

FIG. 16 shows the automated dosing apparatus of FIG. 15 with the filled pocket moved from the fill position, toward the dispense position, with the filled pocket partially overlapping the dispensing opening.

FIG. 17 shows the automated dosing apparatus of FIG. 16 with the powder material emptied from the fill pocket and dispensed into the registered depression.

FIG. 18 shows the automated dosing apparatus of FIG. 17 with an empty depression of the blister sheet moved into registry with the dispensing opening.

FIG. 19 illustrates another embodiment of an automated dosing apparatus for filling a plurality of depressions in a dosing package, including a volumetric dispensing pocket and a tamper.

FIG. 20 shows an elevation sectional view through the automated dosing apparatus and volumetric dispensing pocket of FIG. 19.

FIG. 21 shows an elevation sectional view through the automated dosing apparatus and volumetric dispensing pocket of FIG. 20, with a powder bin and the fill pocket filled with powder material.

FIG. 22 shows the automated dosing apparatus of FIG. 21 with the powder material substantially emptied from the fill pocket and dispensed into the registered depression.

FIG. 23 shows the automated dosing apparatus of FIG. 22 with the tamper extending through the fill pocket and the dispensing opening.

FIG. 24 shows the automated dosing apparatus of FIG. 23 with the tamper retracted and with an empty depression of the blister sheet moved into registry with the dispensing opening.

FIG. 25 illustrates various means for spreading a pile of powder material in a substantially uniform layer by shaking and/or oscillating the depression.

FIG. 26 illustrates a support plate having openings in registry with the pattern of depressions for the blister pack.

FIG. 27 illustrates a support plate having openings in registry with the pattern of depressions for the blister pack, and a vacuum means for securing a blister sheet to the support plate.

DETAILED DESCRIPTION OF THE INVENTION

Definitions

As used herein, the term "depression" refers to a spatial cavity formed into a portion of a packaging for a dosage form. Non-limiting examples of the depression portion of a packaging include a blister, cup, pod, or other packaging receptacle capable of receiving and containing flowable materials such as powder or liquid.

As used herein, "3DP" means three-dimensional printing, three-dimensionally printed or other such conjugation thereof.

As used herein, the term "tamping" pertains to an act of reducing the porosity or pore volume within a volume of a mass of powder under a force that reduces the volume of the mass of powder. Tamping can be effected with a tamper system, whereby a volume of one or more incremental formed layer of powder formed within a depression is shaped and/or reduced.

As used herein, "shaping" refers to the act of altering the shape of one or more surfaces of an incremental layer of a material, or the shape of a plurality of one or multiple layers. The altering of the shape can be of the entire surface or of only a portion of the surface, and typically the upper surface at the step of shaping. The altered shape can be flat or planar, convex, concave, or any other shape as desired. The altered shape of the upper surface can be different from the shape of the lower surface.

A process of the invention can comprise one or more tamping steps, one or more shaping steps, and/or one or more marking steps.

As used herein, a "three-dimensional printing build system" or "3DP build system" generally comprises a powder layering system (region), where a powder material is deposited and/or layered into an incremental powder layer within a depression, and a printing system (region), wherein a binding liquid is applied to the incremental powder layer according to a predetermined pattern thereby forming a partially or fully bound powder layer (an incremental printed layer).

Figure 1:
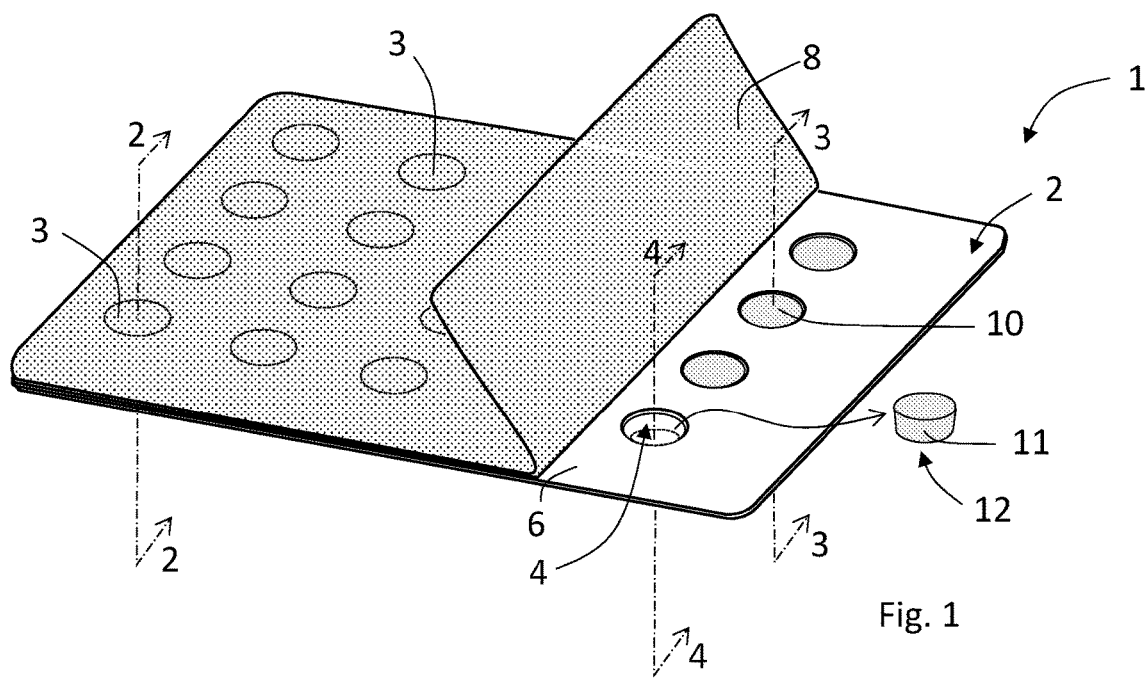
FIG. 1 illustrates a blister pack with a portion of the lidding sheet peeled back, showing dosage forms disposed within the depressions.
Figure 2:
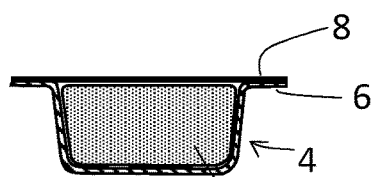
FIG. 2 illustrates a cross-sectional view of a dosage form within a depression covered with the lidding sheet.
Figure 3:
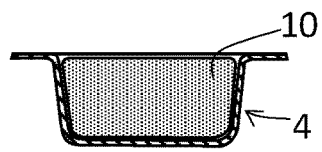
FIG. 3 illustrates a cross-sectional view of a dosage form within a depression, with the lidding sheet removed.

FIG. 1 shows a blister pack 1 including a blister sheet 2 in which a desired number of depressions 4 are formed in a sheet 6 of a desired film or laminate material through conventional cold forming. A lidding sheet 8 is shown sealed to the sheet 6 including at locations 3 over depressions that contain dosage forms 10 (also illustrated in the sectional view of FIG. 2). The front portion of the blister pack 1 illustrates the lidding sheet 8 folded back from over the sheet 6, to illustrate exposing the dosage forms 10 disposed within depressions 4 (illustrated in the sectional view of FIG. 3) or removed from the depressions 4 (illustrated in the sectional view of FIG. 4). The size and shape of the depressions 4 is a matter of choice that can be dictated by the size and nature of the tablet to be formed, as well as other considerations that are well known to those persons skilled in the art. The number and arrangement of the depressions 4 in the blister sheet 2 are a matter of choice or selection that can be based upon the dosage and duration of administration of the tablets, economics, and the type of API active in case of a drug or pharmaceutical tablet, as well as other considerations that are well known to those persons skilled in the art. The film or laminate sheet 6 comprises a formable material into which the one or more depressions can be formed. In one embodiment the film or laminate sheet 6 can comprise a thermoformable plastic layer, for example, polymeric substances including polyamide, polyvinylchloride, polypropylene or other such substances. In another embodiment, the film or laminate sheet 6 can comprise a cold formable metal foil, such as an aluminum film. A laminate material can include two or more layers that can be made of the same or different materials, and the same or different thicknesses. The film or laminated material can have a thickness between 25 and 100 microns (μm).

Figure 4:
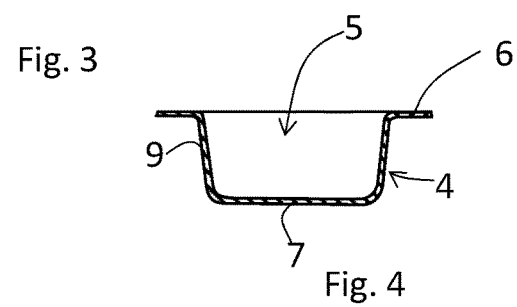
FIG. 4 illustrates a cross-sectional view of a depression from which the dosage form has been removed.

FIG. 4 illustrates a single portion of a blister-type packaging for a dosage form, consisting of a depression 4 formed into the sheet 6 and having a closed end 7 and an outer wall 9 that defines a space 5 within the depression 4. The depressions 4 in the blister sheet 2 are illustrate in a non-limiting embodiment with a circular plan shape and an outer wall tapering inwardly from the sheet toward the closed end 7. Some embodiments of a depression in a blister sheet packaging have elongated shapes, or complex shapes. Some embodiments have outer walls that are rounded, arcuate, or perpendicular with the packaging sheet. A person of ordinary skill would recognize and understand that any embodiment of a packaging material or a depression of any type, shape or size, can be combined, directly and unambiguously, with any other embodiment pertaining to the invention described herein.

FIG. 5 illustrates an initial, though in some embodiments an optional, step of depositing an initial layer 31 of a binding liquid onto the bottom or closed end 7 of the depression 4, to provide binding of initial powder material 20 that is deposited into the depression 4. The initial layer 31 of a binding liquid can be deposited by spraying droplets 30 of the binding liquid, for example from print nozzles 32 of an inkjet printing nozzle assembly 33. An initial layer or film of binding liquid ensures that a bottom surface of the dosage form 10 securely bonds the particles along the bottom surface 12. In some embodiments, an excess amount of binding liquid, more than an amount sufficient to at least bind together the particles of the powder material, is used, to form a wetted coating, which when dried or cured forms a hard, resilient bottom coating. In some embodiments, the binding liquid used to form the wetted coating is a different liquid than the binding liquid used for forming the bound powder layers.

FIGS. 6 through 24 illustrate methods and apparatus for depositing a powder material into one or more depressions of a blister-type packaging.

FIG. 6 illustrates a step of depositing a first predetermined amount 40 of a powder material 20 comprising particles, within the depression 4 or into each of a plurality of depressions 4. The powder 20 is discharged from a feed container or hopper, 22 through a powder-dosing apparatus 24. The powder-dosing apparatus 24 is designed and configured to dispense a predetermined amount 40 of powder from the feed container 22, which can include a predetermined volumetric amount of powder or a predetermined mass amount of powder. In the illustrated embodiment, a predetermined amount of powder 40 is deposited onto the closed end 7 of the depression 4 in the form of a pile 40 of powder. A bottom portion of the first deposited pile 40 of powder 20 is wetted by the optional initial layer 31 of binding liquid, as seen in FIG. 5, to form a coating 50 on the bottom 12 of the dosage form.

In one embodiment, the predetermined amount of powder 40 can be a predetermined volume of a powder material, the powder material having presumably a substantially uniform powder density such that the predetermined volume delivers a substantially fixed mass weight of the powder material. An accurate and reproducible mass weight of a deposited amount of powder material is important to ensure that the finished dosage form, consisting of two or more deposits of the powder material, has a consistent, accurate amount of the total powder material. In an embodiment where the powder material comprises an active ingredient in particulate form, such as a particulate pharmaceutical or drug, and the powder material comprises one or more other particulate materials, it is preferred that the particulate active ingredient does not segregate from the other particulate materials.

In another embodiment, the predetermined amount of powder can be a predetermined mass weight of a powder material. Again, presuming a substantially uniform powder density, the predetermined mass weight delivers a substantially fixed volume of the powder material. In the illustrated embodiment, the predetermined mass weight of a powder material provides a volume of powder material sufficient to form a substantially uniform powder layer of the fixed volume, within the bottom portion of the available space within the depression 4. Depending on the size and shape of the bottom portion of the available space within the depression 4, a first powder layer consisting of a substantially uniform powder layer of a predeterminable depth is formed.

A representative example of a dosing apparatus 24 is shown in FIG. 7 as a manual dosing device 75. The manual dosing device 75 comprises a feed container or hopper 71 containing a bulk supply of powder material 20, an outer cylinder 73 mounted to the bottom of the hopper 71 and having an upper opening communicating with the hopper 71, and a lower opening 173, and an inner cylinder 79 that rotates axially within the outer cylinder 73, as shown by the rotation arrows R-R in FIG. 7. The inner cylinder 79 is configured to rotate within the outer cylinder 73 between a fill rotation position shown in FIG. 8 and a dispensing rotation position shown in FIG. 10. Inner cylinder 79 has a cylindrical fill cavity 77 formed into the cylindrical wall of the inner cylinder 79, which opens into the volume of the feed hopper 71 when rotated to the fill rotation position, as shown in FIG. 8, and opens to the lower opening 173 of the outer cylinder 73 when rotated to the dispensing rotation position, as shown in FIG. 10.

FIG. 8 shows a section view along lines 8-8 of the manual dosing device 75 of FIG. 7. In the fill position, the fill cavity 77 of the inner cylinder 79 communicates with the interior space of the hopper 71 to allow powder 20 to flow by gravity into and completely fill the volume of the fill cavity 77 with a predetermined volume of powder 177. The volume of fill cavity 77 is a predetermined volume for holding a requisite volume of powder material needed for one layer of powder deposition. In some embodiments, the inner cylinder 79 and its fill cavity 77 can be replaced with another inner cylinder having a differently-sized fill cavity for depositing a different predetermined volume of powder. In another embodiment of the invention, the system can include a second (or more) manual dosing device having a fill cavity of a different volumetric size to accommodate the forming of initial and incremental layers of powder of different predetermined volumes, or for accommodating a powder material having a different specific density to achieve a target mass amount of the powder material.

FIG. 9 shows the inner cylinder 79 in an isolated rotation position between the fill rotation position and the dispensing rotation position, where the powder material 177 in the fill cavity 77 is isolated from the hopper 71. FIG. 10 shows the inner cylinder 79 rotated to the dispensing rotation position to discharge by gravity the predetermined volume of powder 177 (dashed lines) from the fill cavity 77, through the opening 173 in the bottom of the outer cylinder 73, and into the bottom of the space 5 of the depression 4 as pile 40 of powder material. Thereafter, the manual dosing device 75 can be repositioned by rotating the inner cylinder 79 and the emptied fill cavity 77 back to the isolated rotation position, and then back to the fill rotation position shown in FIG. 8 for refilling the fill cavity 77 with powder 20. The deposition of powder by gravity into the depression 4 creates a pile 40 of powder over the top surface of a first bound powder layer 61, as shown in FIG. 6, typically though not necessarily in a consistent and reproducible shape, and typically with a tapering shape based on the angle of repose of the powder material. The peak of the pile 40 of powder material is typically beneath the discharge opening 173 of the powder-dosing apparatus 24, with tapering of the powder surface towards the outer walls 9 of the depression 4.

Figure 11:
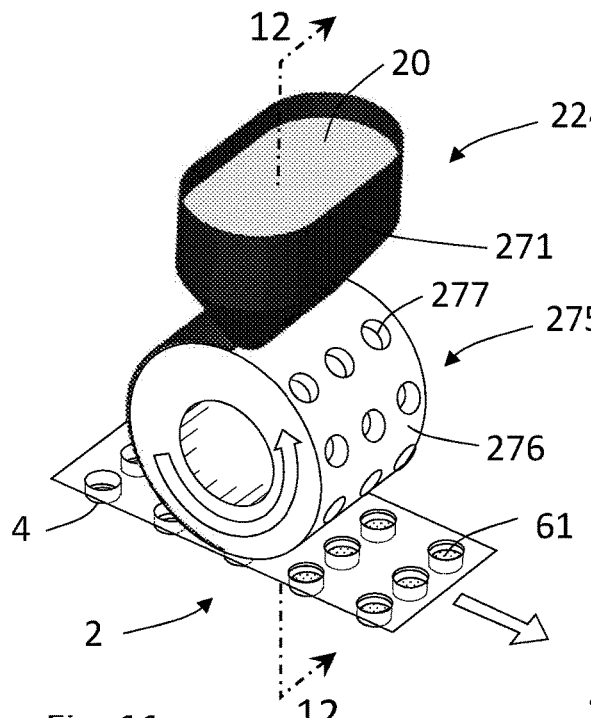
FIG. 11 illustrates a rotary dosing apparatus for dispensing a powder material into depressions in a blister sheet 2.

An example of an automated dosing apparatus for filling a plurality of depressions in a dosing package is a rotary dosing apparatus shown in FIG. 11. The rotary dosing apparatus 224 includes a hopper 271 containing a supply of powder material 20, and a rotary drum 275 having an outer surface 276 in which are formed a plurality of fill cavities 277 in a number sufficient to fill the number of depressions 4 in a blister sheet 2. The blister sheet 2 with a desired number of depressions 4 is moved (arrow) beneath the rotary dosing apparatus 224, in synchronous speed with the rotation of the rotary drum 275 with the ports 277 in registry with the depressions 4.

Figure 12A:
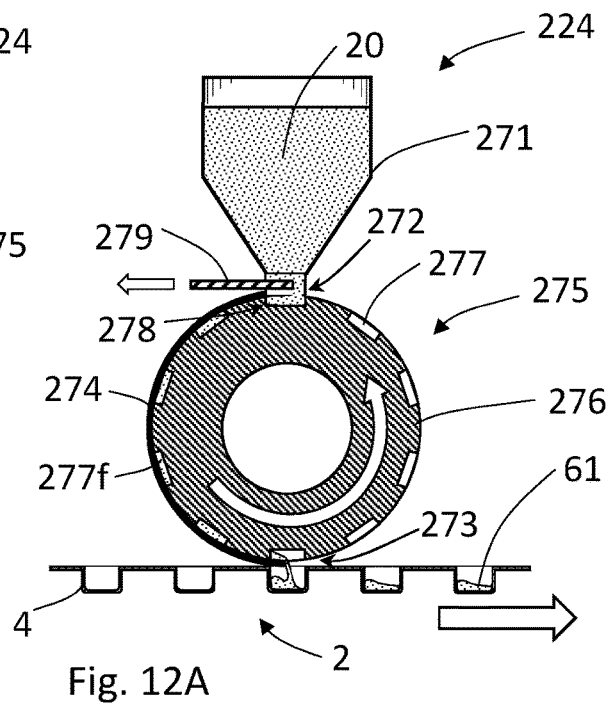
FIG. 12A shows an elevation sectional view through the rotary dosing apparatus and blister sheet of FIG. 11.

The bin 271 includes a plurality, illustrated as three, dispensing ports that feed powder material into the fill cavities 277. FIG. 12A shows a sectional view through the hopper 271 and rotary drum 275, showing a dispensing gate 278. A slide gate 279 dispenses powder material through a dispensing gate 278 disposed at a fill point 272 of the apparatus 224. As the rotary drum 275 rotates, each fill cavity 277 revolves toward the fill point 272. As the fill cavity 277 approaches the fill point 272, the slide gate 279 is pulled open (small arrow) within a slot of the dispensing gate 278 to allow a portion of the powder material to pass through and fill up the fill cavity 277. The slide gate 279 can be oriented to be pulled open transverse to the axis of rotation 100 of the rotary drum 275 (as illustrated), either opposite (or in) the direction of movement of the blister sheet 2, or oriented to be pulled open parallel to the axis of rotation 100.

The rotary dosing apparatus 224 also includes a shell 274 that has an arcuate inner surface that confronts the outer cylindrical surface 276 between the slide gate 279 and the discharge point 273 of the apparatus 224, covering the filled cavities 277f (fill cavities 277 filled with powder material 20) to prevent spillage of the powder material. The leading edge of the shell 274 provides a means for clearing excess powder dispensed into the fill cavity 277, and leveling off the surface of the powder within the filled cavity 277f.

In some embodiments of a rotary dosing apparatus, a vacuum system can be included that applies a vacuum upon the inside surface of the fill cavities 277 to assist in maintaining the powder material charged into the fill cavities 277.

Figure 12B:
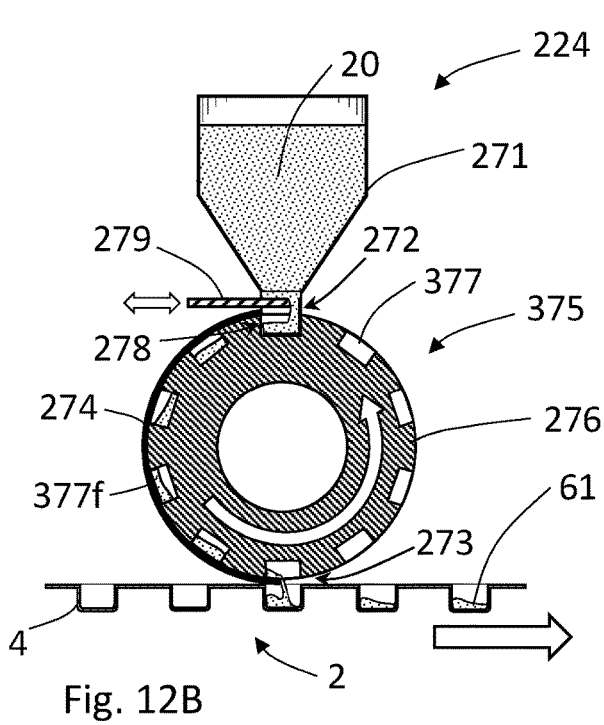
FIG. 12B shows an elevation sectional view through another embodiment of a rotary dosing apparatus and blister sheet.

In some embodiments, each fill cavity is sufficient in size and depth to hold and dispense a layer of powder material 20 into each depression 4 of a blister sheet 2, forming a powder layer 61. FIG. 12B illustrates a rotary dosing apparatus 375 in which each fill cavity 377 is sufficient in size to hold a volume of powder that is in excess of the amount of powder needed to form a powder layer in a depression. In such embodiments, the apparatus 224 also includes a volumetric dispensing pocket to meter a predetermined volume of powder material into the over-sized fill cavity. An example of a volumetric dispensing pocket is illustrated in FIGS. 13-18, and discussed herein after.

In some embodiments, the volumetric rate of powder material into the fill cavities 377 can be throttled using a slide gate or other well-known means for restricting the flow of powder material from the bin 271. A non-limiting example of a restricting means is the dispensing gate 278.

After each of the filled cavities 277f (or 377f) deposits its powder material into an empty depression 4 of the blister sheet 2, the fill cavities 277 (or 377) of the rotary drum 275 and the blister sheet 2 advance in registry at the same linear speed. Once emptied, the fill cavities advance toward the fill point 272. In some embodiments, the rotation of the rotary drum 275 the advancement of the blister sheet 2 proceed constantly, and in some embodiments the rotation of the rotary drum 275 the advancement of the blister sheet 2 are temporarily halted when the fill cavities arrive at the fill point and/or the discharge point.

Figure 13:
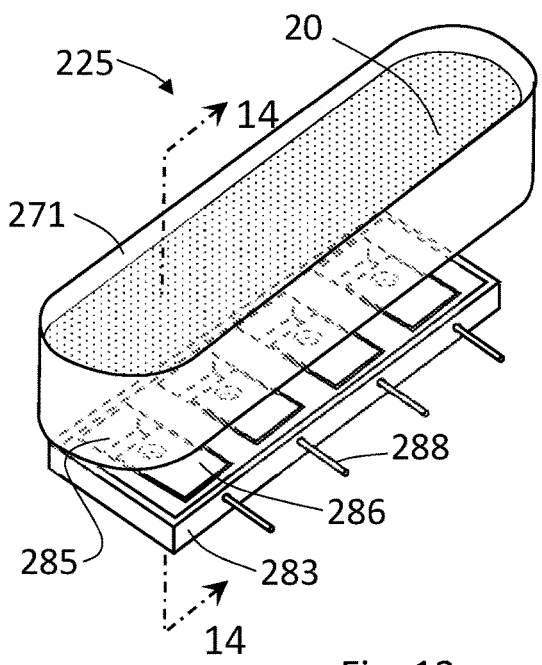
FIG. 13 illustrates an automated dosing apparatus for filling a plurality of depressions in a dosing package, including a volumetric dispensing pocket.

FIGS. 13-18 illustrate another embodiment of an automated dosing apparatus 225 for filling a plurality of depressions in a dosing package. FIG. 13 shows an elongated bin 271 containing a powder material 20. The bin 271 is oriented along the width of the blister sheet 2, transverse to the direction of movement of the blister sheet 2 beneath the dosing apparatus 225. FIG. 14 illustrates an empty bin 271 having a bottom dispensing opening that feeds a volumetric dispensing pocket 282. The volumetric dispensing pocket 282 includes a support frame 283 that has an elongated cavity 285 and a dispensing opening 284 at a distal end. A pocket gate 286 is disposed within the elongated cavity 285, and has a pocket bore 287 in a distal portion, and a manipulation means extending from the proximal portion, illustrated as a shaft 288 that extends through a rear opening in the support frame 283. The pocket gate 286 is movable within the elongated cavity 285, via the manipulation means, between a fill position shown in FIG. 15, and a dispensing position, shown in FIG. 17. In FIG. 15, powder material 20 flows under gravity to completely fill the pocket bore 287. Concurrently, the blister sheet 2 is position beneath the volumetric dispensing pocket 282 to register an empty depression 4 below the elongated cavity 284 of the support frame 283.

In FIG. 16, the manipulation means, illustrated as a force exerted upon the shaft 288, moves (slides) the pocket gate 286, and the filled pocket bore 287, distally. As the pocket gate 286 moves distally, the upper surface of the proximal portion of the body of the pocket gate 286 covers and closes off the bottom dispensing opening of the elongated bin 271. As the pocket gate 286 continues to move distally, the filled pocket bore 287 of the pocket gate 286 moves toward registry with the dispensing opening 284. As the filled pocket 287 begins to overlap and move into registry with the dispensing opening 284 of the frame, shown in FIG. 16, the powder material with the pocket bore 287 begins to empty out, through the dispensing opening 284, and in the depression 4 in registry. Once the pocket gate 286 moves into registry with the dispensing opening 284, as shown in FIG. 17, essentially the entirety of the powder material has fallen from the pocket bore 287, through the dispensing opening 284 and into the depression 4. Once the pocket bore 287 is emptied, the blister sheet 2 is advanced to move the next empty depression 4 into registry beneath the dispensing opening 284, as shown in FIG. 18. Simultaneously or contemporaneously, the manipulation means, illustrated as a force exerted upon the shaft 288, moves (slides) the pocket gate 286, and the emptied pocket bore 287, proximally, and back into the fill position shown in FIG. 15.

It should be understood that the registering and filling of depressions, and the movement of the pocket bores between the filled and dispensing positions, occurs simultaneously or contemporaneously in the other depressions and volumetric dispensing pocket 282 laterally along the elongated bin 271.

FIGS. 19-24 illustrate another embodiment of an automated dosing apparatus 226 for filling a plurality of depressions in a dosing package. In FIG. 19, similarly to the embodiment shown in FIG. 13, an elongated bin 271 containing a powder material 20 is oriented along the width of the blister sheet 2, transverse to the direction of movement of the blister sheet 2 beneath the dosing apparatus 226. FIG. 20, similarly to the embodiment shown in FIG. 14, illustrates an empty bin 271 having a bottom dispensing opening that feeds a volumetric dispensing pocket 292, similar to the volumetric dispensing pocket 282. The volumetric dispensing pocket 292 includes a support frame 293 that has an elongated cavity 295 and a dispensing opening 294 at a distal end. A pocket gate 296 is disposed within the elongated cavity 295, and has a pocket bore 297 in a distal portion, and a manipulation means extending from the proximal portion, illustrated as a shaft 298 that extends through a rear opening in the support frame 293. The pocket gate 296 is movable within the elongated cavity 295, via the manipulation means, between a fill position shown in FIG. 21, and a dispensing position, shown in FIG. 22. In FIG. 21, powder material 20 flows under gravity to completely fill the pocket bore 297. Concurrently, the blister sheet 2 is position beneath the volumetric dispensing pocket 292 to register an empty depression 4 below the cavity 294 of the support frame 293.

In FIG. 22, the manipulation means, illustrated as a force exerted upon the shaft 298, moves (slides) the pocket gate 296, and the filled pocket bore 297, distally, and toward and into registry with the dispensing opening 294. As the pocket gate 296 moves distally, the upper surface of the proximal portion of the body of the pocket gate 296 covers and closes off the bottom dispensing opening of the elongated bin 271. Once the pocket gate 296 moves into registry with the dispensing opening 294, as shown in FIG. 22, typically the entirety of the powder material has fallen from the pocket bore 297, through the dispensing opening 284 and into the depression 4. In some embodiments and circumstances, a portion of the powder material within the emptied pocket bore 297 may remain, clinging or adhering to the rim of the pocket bore 297. To ensure the entirety of the powder material is dispensed into the depression, a tamper 88 is provided having a rim 89 and an under surface 87, disposed vertically above and in axial registry with the dispensing opening 294. As the tamper 88 is lowered in registry through the pocket bore 297 and the dispensing opening 294, the rim 89 and under surface 87 clear all powder material from within the pocket bore 297, and into the depression 4, as shown in FIG. 23. In some embodiments, the rim 89 of the tamper 88 extends sufficiently to have the under surface 87 extend into the depression 4 and into contact with the powder layer 61. In some embodiments, the tamper 88 is sufficient to level and/or tamp the powder layer, as described in further detail herein below.

Once the pocket bore 297 is emptied, the blister sheet 2 is advanced to move the next empty depression 4 into registry beneath the dispensing opening 294, as shown in FIG. 24. Simultaneously or contemporaneously, the manipulation means, illustrated as a force exerted upon the shaft 298, moves (slides) the pocket gate 296, and the emptied pocket bore 297, proximally, and back into the fill position shown in FIG. 21.

In some embodiments, a 3DP system and apparatus can include a second or more dosing apparatus for dispensing a second powder material, including a different second powder material, into the depressions, for forming a dosage form that contains two (or more) sources, types and compositions of powder material.

Other non-limiting examples of a mechanical dosing and/or metering apparatus is described in U.S. Pat. Nos. 9,409,699 and 9,828,119, and US Patent Publications 2017/0322068 and 2018/0031410, the disclosures of which are incorporated by reference in their entireties. Piezo-needle dispensing apparatuses dispense a powder actuated by passing the powder material down a stainless-steel tube using a piezoelectric actuator-driven standing wave. At the dispensing tip of the needle, the standing wave serves to eject the powder material. These devices are effective at delivering low and fixed levels of powder material, delivered with precision.

Other non-limiting examples of a mechanical dosing and/or metering apparatus can include a gravimetric powder dispensing/powder dosing apparatus available from ChemSpeed Technologies (https://www.chemspeed.com/flex-powderdose/), the disclosures of which are incorporated by reference in its entirety.

In some embodiments, the method and system include a means for leveling a pile of powder material within a depression. FIG. 25 illustrates a step of leveling a pile 40 of a predetermined amount of a powder material 20, within the depression 4, into a substantially uniform layer of powder 41. A pile 40 or other shaped deposit of powder material 20 is transformed into a substantially uniform layer 41 of powder using a leveling means. In the illustrated embodiment of FIG. 25, a leveling means includes a method comprising any one or a combination of laterally, orbitally, and vertically oscillating the depression 4, and the pile 40 of powder contained therein, with a frequency and velocity sufficient to cause the pile 40 of powder to disperse and be spread outwardly over the entire bottom area of the space 5 of the depression 4, and in some embodiments, into a substantially uniform layer 41 of powder. The method forms a first substantially uniform layer 41 of powder, having a predeterminable layer thickness or height of "h". In a manual system, the packaging and the depression portion thereof can be shaken manually or with a vibrating table. Non-limiting examples of mechanical vibrating tables, conveyors are available from the Tinsley Equipment Company, available at https://www.tinsleycompany.com/bulk-process-equipment/vibratory-process-equipment/vibrating-tables/, the disclosure of which is incorporated by reference.

In some embodiments, a layer of powder material that is prepared within a depression has a flat, planar surface, parallel with the base of the depression. In some embodiments, a layer of powder material that is prepared within a depression can have a uniform thickness with a tolerance. In such embodiments, the thickness of a layer of powder material that is slightly non-uniform in thickness but within the tolerance can be bound with a binding liquid into a bound-powder dosage form. In some embodiments, the non-uniformity in level of the powder material layer can be defined by the variance in thickness of the powder layer from a weight average or target thickness. A minimum thickness in the powder layer and a maximum thickness in the powder layer can have a variance relative to the weight average thickness, where the variance is up to about 25% variance. In some embodiments, the variance is up to about 20% variance, up to about 15%.variance, and in some embodiments, up to about 10% variance, and the variance can be at least 5%, at least 10%, at least 15%, or at least 20% variance. For example, a layer of powder material having a weight average (target) thickness of 0.50 mm can have a thickness with a tolerance of 20%, wherein the powder layer has a minimum and maximum thickness from 0.40 mm to 0.6 mm, while the binding of the powder material with a binding liquid is still effective. In another example, a layer of powder material having a weight average (target) thickness of 1.0 mm can have a thickness with a tolerance of 15%, wherein the powder layer has a minimum and maximum thickness from 0.85 mm to 1.15 mm, while the binding of the powder material with a binding liquid is still effective. FIG. 26 illustrates a support plate 15 that can be used to secure and support the one or more depressions 4 of the blister pack 1, including, but not limited to, during powder deposition and layering, binding liquid deposition, solvent removal, and any other process step of the method and system. Ports or openings 16 in the support plate 15 provide a receptacle for receiving and supporting a depression 4 and the blister pack 1 upon the upper surface 17 of the support plate 15. In some embodiments, a pattern of depressions can be registered with a pattern of openings 16 in a support plate 15. In some embodiments, the pattern of openings 16 includes a plurality of rows and a plurality of columns. In some embodiments, the openings 16 extend into and through the entire thickness of the support plate 15. In some embodiments, the openings 16 extend into and only partially through the thickness of the support plate 15, to provide a blind hole.

FIG. 27 illustrates an embodiment of a support plate 115 that includes a pattern of openings 116 through the upper surface 117, forming blind holes into the support plate 115. The support plate 115 has three columns and four rows of blind holes 116, and a series of longitudinal entry bores 118 extending from an end edge 114 of the support plate 115, and intermediate bores 119 extending through the thickness along the column of four blind holes 116, and through the material between each of the adjacent openings 116, thereby placing the entry bores 118 and intermediate bores 119 into communication with each blind opening 116 in the column. Application of a vacuum to the entry bores 118 communicates with each blind opening 116 via the intermediate bores 119, to draw and secure the blister pack 1 to the upper surface 117 of the support plate 115.

Figure 28:
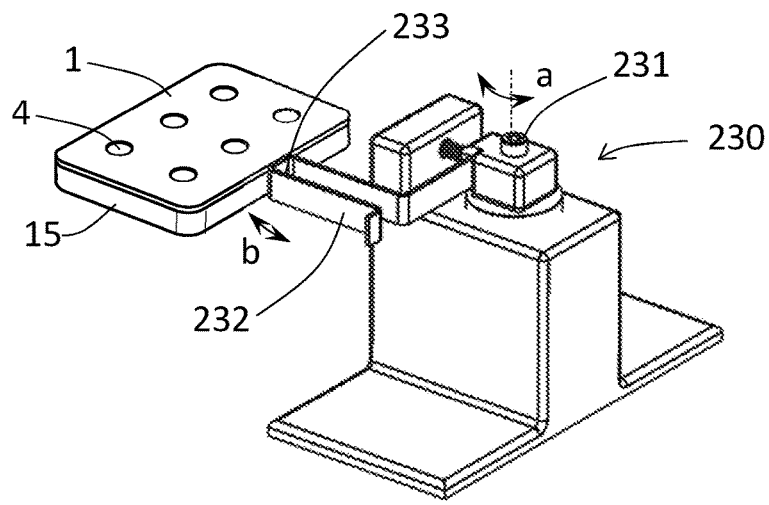
FIG. 28 illustrates a laterally-oscillating vibratory apparatus to level powder material in depressions of a blister sheet.

FIG. 28 illustrates a non-limiting example of a powder leveling means, as a vibratory apparatus 230 for use in providing lateral oscillating of a depression 4 within blister sheet 1. In the illustrated embodiment, the blister sheet 1 is supported within a support plate 15. The apparatus has a tapping arm 232 having a u-shape and having a proximal end attached to a pivoting post 231 that oscillates around an axis "a", causing a base 233 of the U-shaped tapping arm 232 to oscillate laterally "b" into a side edge of the support plate 15. The lateral tapping provides leveling and improves the uniformity of the powder material into a layer of powder within the depression. The frequency and degree of rotative oscillation "a" of the pivoting post 231 is controlled to provide a frequency and impact force of the oscillation of the base 233 against the support plate 15 to provide effective leveling of the powder layer, without ejecting powder out of the depression or drifting the powder unevenly within the depression.

An alternative apparatus for leveling a pile of powder into a substantially uniform layer of powder within a depression is shown in FIGS. 29-32.

FIGS. 29 through 32 illustrate an alternative leveling apparatus for leveling a pile 40 of powder 20 into a substantially uniform layer of powder within a depression 4. A leveling device 80 is shown disposed in a position above an open-ended depression 4 in which a pile 40 of a predetermined quantity of powder material 20 has been deposited onto the center of a first bound powder layer 61. The leveling device 80 is employed to form a substantially uniform layer of the powder material, from the non-uniformly placed pile 40 of powder material. The layering device 80 includes a vertical rotor shaft 82 that is driven by a powered rotating means (not shown). Non-limiting examples of such powered rotating means include servo motors. A powder level member extends horizontally, and radially from the bottom of the rotor shaft 82, to a distal end that is substantially the radius of the depression 4. The powder level member rotates around the axis of the rotor shaft 82 while being lowered down into the pile 40 of powder material to form the substantially uniform layer of powder within the depression 4.

Figure 29:
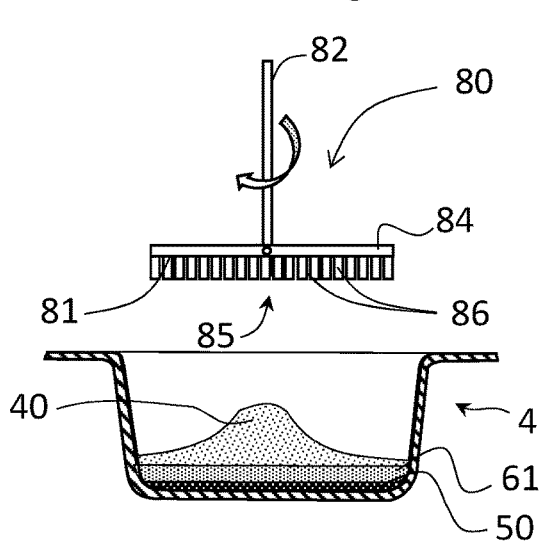
FIG. 29 illustrates a brush assembly for use in leveling the pile of powder within the depression of FIG. 28.

As shown in FIG. 29, the powder level member can include a brush assembly comprising a circular disk 84 attached at its center to the lower end of the rotor shaft 82, and is configured to rotate about the axis of the rotor shaft 82. In one non-limiting embodiment, the circular disk 84 includes a plurality of brushes 86 attached to and extending down from an under surface 81 of the circular disk 84. The plurality of brushes 86 are typically positioned in a pattern to maintain the center of gravity of the circular disk 84 at its attachment point with the rotor shaft 82. In an alternative embodiment, a single circular pad can be attached to the lower surface 81 of the circular disk 84. The plurality of layering brushes 86 are made of a material that avoids adhesion of the particles of the powder material, to avoid sticking during operation. In an embodiment, the plan-view diameter prescribed by the plurality of layering brushes 86 is the same or substantially the same diametric size as the plan-view surface area of bottom of the space 5 within the depression 4.

The rotor shaft 82 can also be assembled integrally within a housing or shroud (not shown), that extends around the outer periphery of the circular disk 84, to create a dust barrier during the leveling of the powder material.

Figure 30:
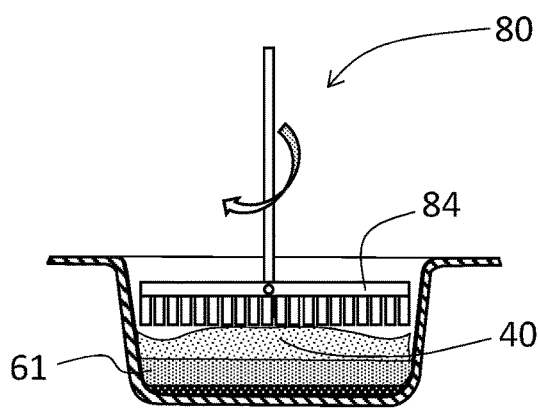
FIG. 30 illustrates the brush assembly of FIG. 29 being lowered into the pile of powder.
Figure 31:
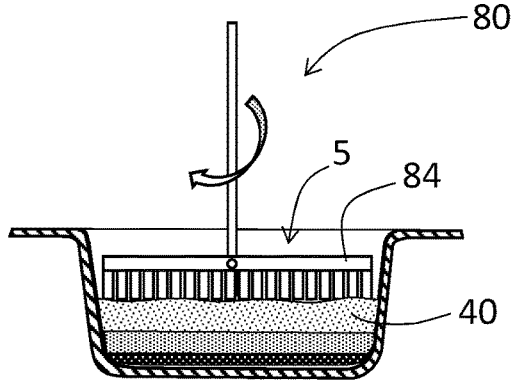
FIG. 31 illustrates the brush assembly of FIG. 29, flinging the particles of the powder radially outward toward the wall of the depression.
Figure 32:
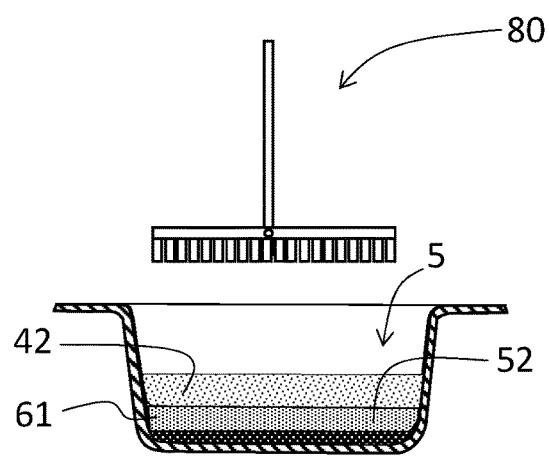
FIG. 32 illustrates the brush assembly removed from within the depression after the pile of powder has been formed into a substantially uniform layer of powder.

As shown in FIGS. 30 and 31, as the brush assembly is rotated and lowered into the depression 4, the plurality of brushes or paddles 86 in the central area 85 of the rotating circular disk 84 contact the peak and the upper portion of the pile 40, flinging the particles of the powder 20 partially and radially outward towards the wall 9 of the depression 4. Once the rotating circular disk 84 is lowered toward an endpoint height shown in FIG. 31, any elevated portion of the pile 40 of the powder material in the center of the depression 4 has been flung or dispersed toward the wall 9, and the top surface of the powder material in the pile 40 becomes substantially flattened to a plane, to form the substantially uniform powder layer 42. The type and resilience of the brushes or other material contacting the particle of the powder, the rotation speed of the rotating circular disk 84, and the rate of descending of the leveling device 80 down into the depression, should be selected and controlled to avoid flinging excessive amounts of the particles to the inside surface of the wall 9 of the depression, which could cause excessive buildup of powder along the wall 9. Once the substantially uniform layer 42 of powder material has been formed, the layering device 80 can be raised out of the space 5 within the depression 4 as shown in FIG. 32.

In alternative embodiments, the powder level member can include a single horizontal member, including using a blade or a bar.

In another embodiment, the powder level member can have a curvature within the plane of rotation.

In another embodiment, the powder level member can have a lower edge that is curved and non-linear, for example, concave or convex, in order to sweep the surface of the pile of powder material into a layer of powder material with the same surface profile.

In some embodiments, the dosing apparatus 24 can comprise an apparatus that both dispenses a predetermined amount of the powder material and forms the powder into a substantially uniform layer of powder within the depression. An example of such an apparatus is shown in FIGS. 33-41.

FIGS. 33 through 38 illustrate an alternative apparatus that both dispenses a predetermined amount of the powder material 20 and forms the powder into a substantially uniform layer of powder within the depression 4. The illustrated layer depositing apparatus 90 can perform simultaneously the step of dispensing the predetermined amount of the powder material 20, and the step of forming the powder into a substantially uniform layer of powder within the depression 4. An example of a layer depositing apparatus is described in U.S. Pat. No. 10,071,372 and U.S. Patent Publication 2017/0312179, the disclosures of which are incorporated herein by reference in their entireties.

Figure 33:
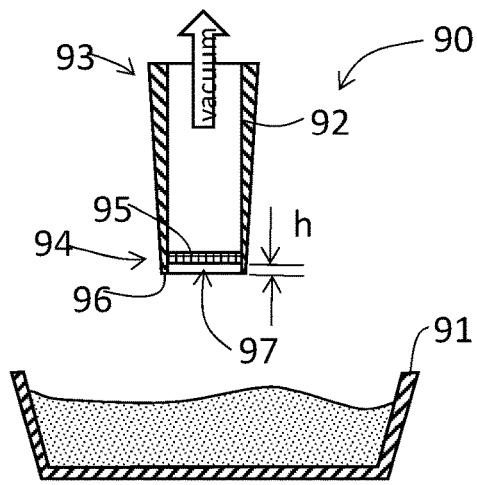
FIG. 33 illustrates a layer depositing apparatus positioned to collect an amount of powder material from a powder hopper.

The layer depositing apparatus 90 is shown in FIG. 33 in position to collect a requisite volumetric amount of powder material from a powder hopper 91 filled with powder. The layer depositing apparatus 90 comprises a suction cylindrical body 92 having an outlet, suction end 93, and an inlet, powder end 94 with an inlet rim 96. Positioned within the body 92 at the powder end 94 is a porous plate 95 that extends across the cross-section of the interior of the body 92. The porous plate 95 can be a woven or nonwoven screen material, or a material having porosity, having a multiplicity of passages leading from its inlet-facing surface to its vacuum-facing surface to form an air-porous medium. The passages are sized sufficiently small to allow free flow of air, while preventing the powder material 20 from entering therein during operation.

The inlet-facing surface of the porous plate 95 is positioned axially at a distance or depth "h" from the inlet rim 96 to define a cylindrical powder take-up volume 97. In one embodiment, the axial position of the porous plate 95 can be moved toward or away from the inlet rim 96 to predeterminably vary the cylindrical powder take-up volume 97, to achieve the predetermined amount of powder materials for forming a substantially uniform layer of powder.

Figure 34:
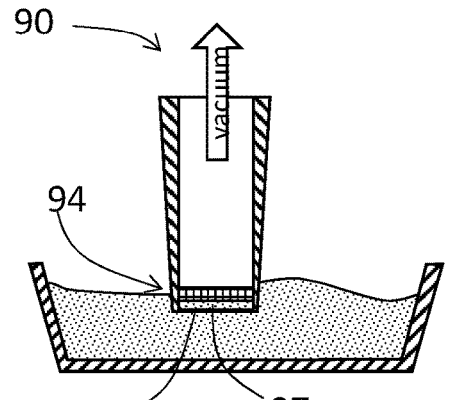
FIG. 34 illustrates a vacuum applied to the interior of the layer depositing apparatus of FIG. 33 to fill the inlet end with a volume of powder from the powder hopper.

As also shown in FIG. 34, a suction is applied to the interior of the body 92 by a remote vacuum source, as indicated by the arrow with the word "vacuum". The vacuum source can be regulated by any known device in the art that can provide a controllable amount of vacuum. The vacuum in the body 92 results in an intake of air through the inlet end 94 that passes through the porous plate 95.

Figure 35:
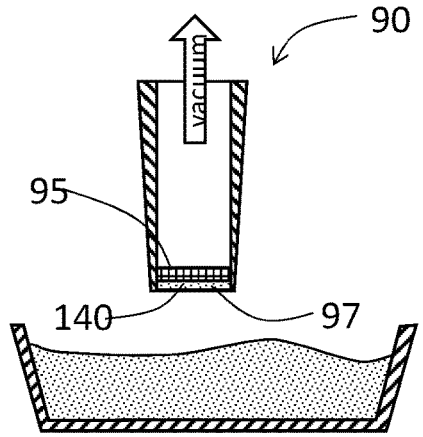
FIG. 35 illustrates the applied vacuum retaining the volume of powder within the inlet of the layer depositing apparatus after the layer depositing apparatus is raised from the powder hopper.

FIG. 34 shows the step of the filling the powder take-up volume 97 with powder 20 by placing the inlet end 94 into the powder hopper 91. The vacuum causes the incoming air to draw the particles of the powder material 20 from the trough 91 into the inlet end 94, where they are pulled and accumulated within into the powder take-up volume 97. So long as the vacuum is sustained, the volume 140 of powder within the powder take-up volume 97 remains drawn toward the porous plate 95 by the incoming air as the layer depositing apparatus 90 is removed from the powder hopper 91, as shown in FIG. 35, and moved to a position over and above the depression 4, as shown in FIG. 36.

Figure 36:
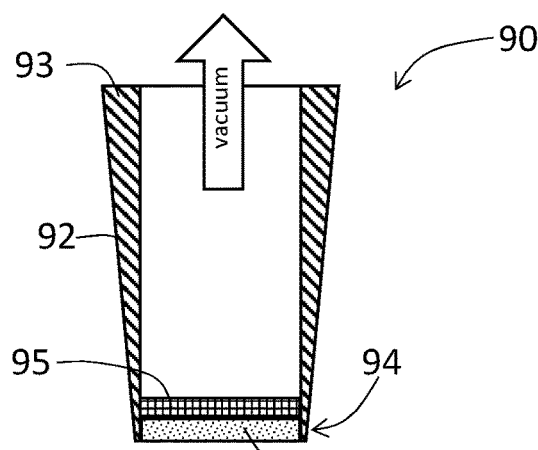
FIG. 36 illustrates the layer depositing apparatus retaining the volume of powder, while positioned above a depression.
Figure 37:
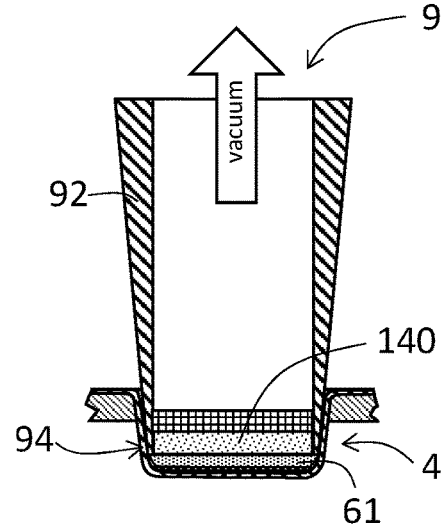
FIG. 37 illustrates the layer depositing apparatus with the volume of powder retained in the inlet, positioned within the depression.
Figure 38:
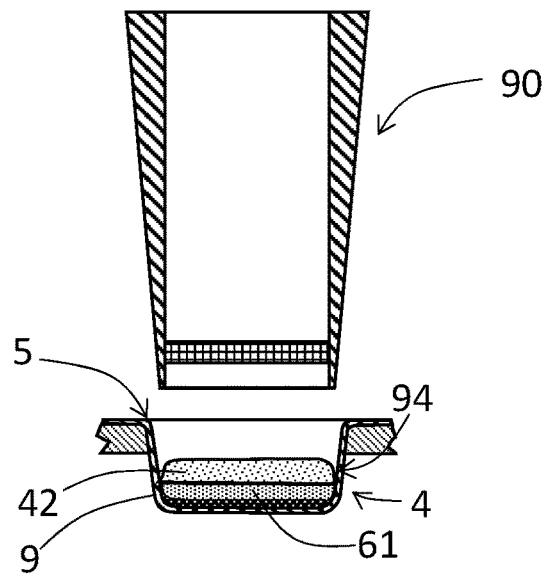
FIG. 38 illustrates the volume of powder deposited within the depression as a uniform layer of powder after the vacuum is removed and the layer depositing apparatus is raised out of the depression.

FIGS. 36-38 illustrate the filling device 90 depositing the volume 140 of powder material 20 into the space 5 of the depression 4. In the illustrated embodiment, the inlet end 94 of the body 92 is configured to be inserted down into the depression 4 during powder deposition and layering. In one embodiment, as shown in FIG. 37, the inlet end 94 of the body 92 is placed just above the last bound powder layer, here, bound powder layer 61, within the depression 4 during powder deposition and layering. As the inlet end 94 is lowered toward the last bound powder layer 61, the application of vacuum is carefully controlled and reduced to reduce the risk that the incoming air flow will damage or disturb the matrix of powder and binder of the bound powder layer 61. When the application of vacuum to the body 92 is removed, the amount 140 of the powder 20 within the powder take-up volume 97 "falls" by gravity onto the upper surface of the last, first bound powder layer 61, forming a second layer 42 of powder as shown in FIG. 38 as the filling device 90 is drawn upward and away from the depression 4.

The body 92 can be configured with a thin and/or tapered wall at the inlet end 94 to minimize the space that the wall occupies between the deposited amount 42 of powder and the inside of the wall 9 of the depression 4. Notwithstanding, an excessive thickness of the wall at the inlet end 94 can result in the lateral diameter (width) of the deposited powder layer 42 to be smaller than the diameter (width) of the inside walls 9 of the depression, which can cause the peripheral wall of the deposited layer 42 of powder to fall away into the gap therebetween as shown in FIG. 38.

In an alternative embodiment, the interior diameter of the powder take-up volume 97 can be matched to the same diameter as the diameter of the inside walls 9 of the depression 4 at the bottom of the space 5. In this embodiment, though not shown, the inlet end 94 of the body 92 is position well above the last bound powder layer 61 within the depression 4. When the application of vacuum to the body 92 is removed, the amount 140 of the powder 20 within the powder take-up volume 97 will fall a short distance by gravity onto the upper surface of the last bound powder layer 61, with the powder area matching the top surface area of the last bound powder layer 61. While this embodiment avoids the gap of the aforementioned embodiment, the free-falling of the powder volume through an airspace can create turbulence that can affect the uniformity of resulting deposited layer of powder.

Figure 39:
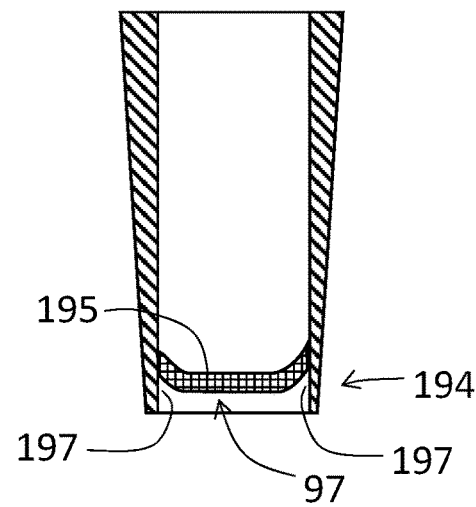
FIG. 39 illustrates an alternative embodiment of a layer depositing apparatus, providing additional powder volume at the periphery of the powder take-up volume.
Figure 40:
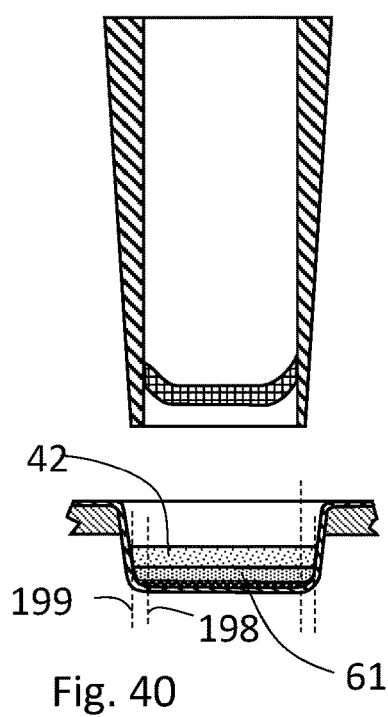
FIG. 40 illustrates the layer depositing apparatus of FIG. 39, positioned within the depression.
Figure 41:
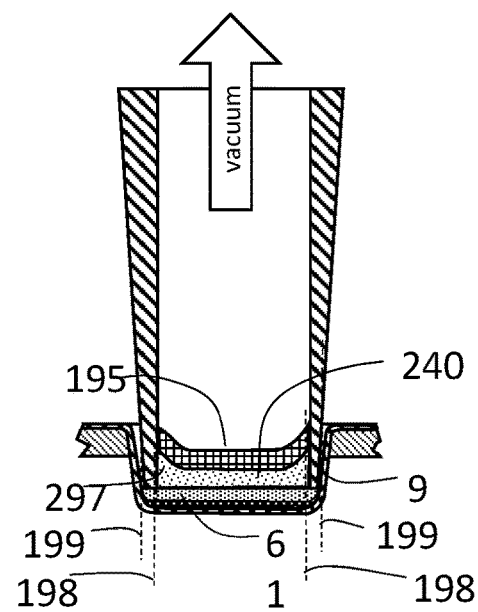
FIG. 41 illustrates the volume and the additional peripheral volume of powder deposited within the depression as a uniform layer of powder after the vacuum is removed and the layer depositing apparatus is raised out of the depression.

An alternative embodiment shown in FIGS. 39-41, to address the issue of the gap of the earlier embodiment, while avoiding the issues caused by the free-falling of the volume of powder onto the top surface of the last bound powder layer 42. In another embodiment, a porous plate 195 shown in FIG. 39 is configured to have an upturned annular periphery deposition, which creates an additional annular powder volume 197 at the periphery of the powder take-up volume 97, and which allows an uptake of powder 240 within the powder uptake volume 197 to include an additional annular amount of powder 297 within the volume 197. As shown in FIG. 40, with the inlet end 194 placed just above the last bound powder layer 61 within the depression 4, the vertical dashed lines 198 that show the outside diameter of the additional powder within additional annular powder volume 197, lie inboard the inside diameter of the wall 9 of the depression 4 shown by dashed lines 199. Nevertheless, as a result of the annular powder 297 within the additional annular powder volume 197, the annular gap between the diameters 198 and 199 is sufficiently filled, resulting in depositing of a substantially uniform powder layer 42 as shown in FIG. 41.

Figure 42:
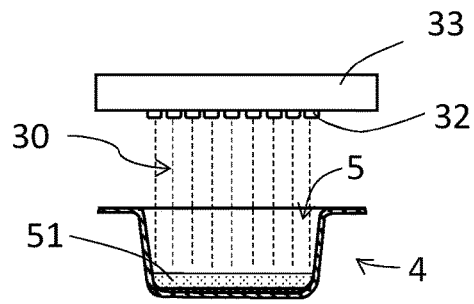
FIG. 42 illustrates applying a binding liquid onto the uniform layer of powder to form a wetted powder layer.

FIG. 42 shows a step of applying a binding liquid onto the space 5 and onto the first layer 41 of powder (FIG. 25). In a preferred embodiment, the binding liquid is applied using 3D printing methods and techniques, such as those described in U.S. Pat. Nos. 6,471,992, 6,945,638, 7,300,668, 7,875,290, and 8,088,415, the disclosures of which are incorporated by reference in their entireties. In the illustrated embodiment, a first predetermined quantity of binding liquid is deposited by spraying droplets 30 of the liquid from the print nozzles 32 of the inkjet printing nozzle assembly 33. The droplets 30 of binding liquid bind particles of the powder material into a cohesive powder-liquid matrix, forming a first layer of wetted powder 51 in a substantially uniform layer.

Figure 43:
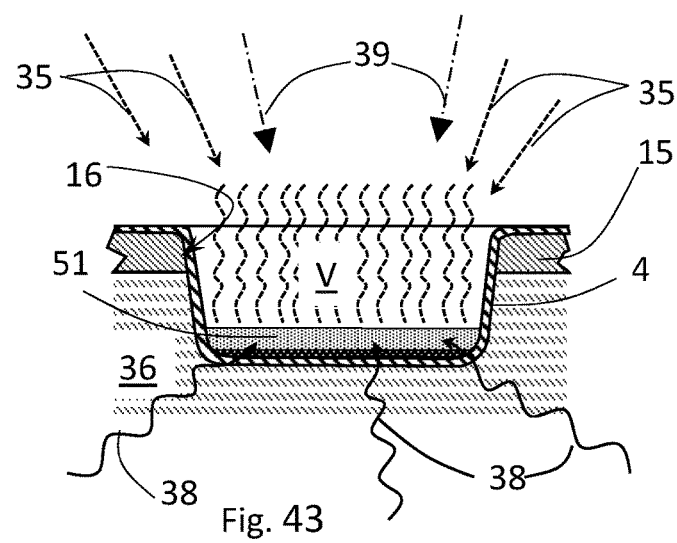
FIG. 43 illustrates several means for applying heat to the wetted powder layer to remove excess solvent liquid, for drying the wetted powder layer and forming a bound powder layer.

In a typical embodiment, the binding liquid includes an amount of a solvent that remains in excess in the resulting wetted powder layer 51, and is preferably removed to form a finished bound powder layer. FIG. 43 shows a depression 4 disposed within a port or opening 16 of a support plate 15 during the process of solvent removal from a wetted powder layer.

A liquid removal system is provided and is adapted to receive one or more blister sheets having one or more layers of wetted powder, or completed 3DP dosage forms, contained within depressions, to remove a liquid there from. A liquid removal system can be a process area through which one or more of the blister sheets are conducted. For example, the liquid removal system can remove or reduce liquid from the incremented printed layers of an in-process 3DP form. Alternatively, the liquid removal system can be another process area not directly associated with the three-dimensional printing system, such as a temporary retaining or storage area wherein three-dimensionally printed blister sheets are placed and dried under ambient conditions. In some embodiments, a liquid removal system is one or more dryers.

FIG. 43 illustrates several means for heating or applying heat to the wetted powder layer 51 formed within the depression 4 to remove excess solvent liquid, generally by evaporation of the excess liquid solvent to a gas or vapor that is carried away from the drying powder layers. The illustrated means for removing liquid solvent can include various forms of heating the excess solvent in the wetted powder layer, to evaporate the excess solvent liquid into a gas or vapor V. The illustrated means can be selected from one or more of: convective heat transfer using heated air 35 that is passed over or down toward the wetted powder layer 51; conductive heat transfer using a heating liquid such as a heated liquid 36 or heated air on the underside of the depressions 4, to conduct heat 38 through the sheet material of the depression 4 and into the wetted powder layer 51; and irradiative heating using infrared radiation 39 from a suitable infrared light source that passes down into the depression and/or through the sheet material of the depression 4 and into the wetted powder layer 51, for example as described in U.S. Pat. Nos. 6,990,748, 6,047,484, and 4,631,837, the disclosures of which are incorporated herein by reference in their entireties.

In some embodiments, a drying apparatus includes a multiplicity of infrared light emitting sources arranged in a pattern, for emitting infrared energy toward an upper surface of a blister sheet 1. The blister sheet 1 including wetted powder material disposed within depressions is passed into a housing and positioned at determined coordinates. In some embodiments, the pattern and coordinates of the upper surface of the wetted powder material is detected and mapped to form a drying profile. The infrared (IR) light sources are illuminated and controlled to emit the IR light exclusively at the upper surfaces of the wetted powder material. The time and intensity of the IR light emitted is maintained to heat and evaporate the upper surfaces and to evaporate moisture and other solvents from the volume for the wetted powder material. In some embodiments, the IR light emitted onto the wetted powder is controlled using a mask that has a pattern of shaped openings to permit passage of the IR energy. In some embodiments, the light emitted through the mask is focused using refractive material, for example, a lens. In some embodiments, IR light source includes a high-resolution IR light emitter, controlled to emit a pattern of IR light.

Figure 44:
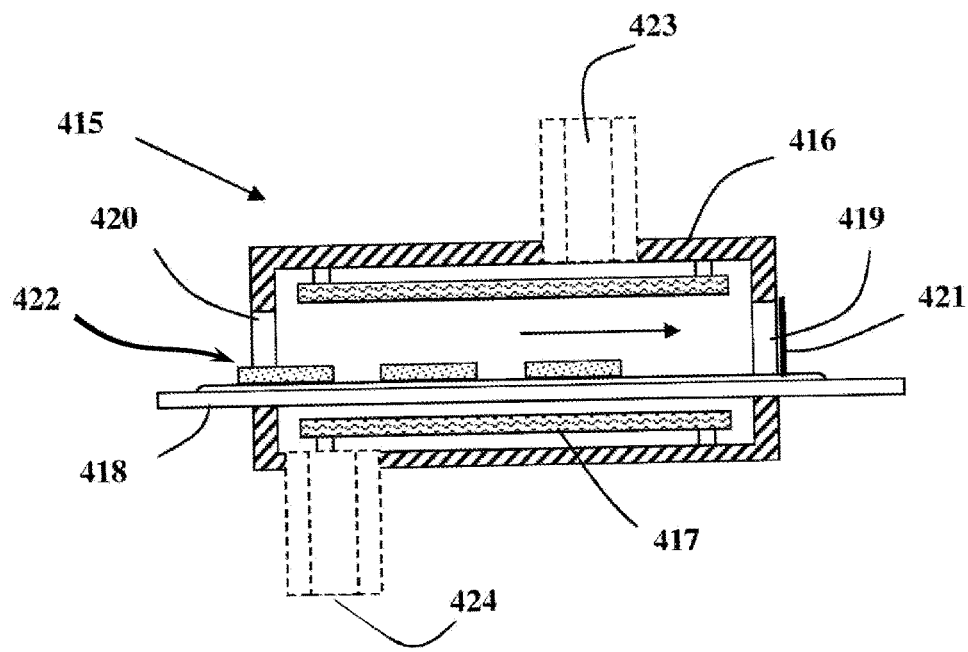
FIG. 44 illustrates a heated air dryer for evaporating moisture and solvent from wetted powder layers.

FIG. 44 illustrates an embodiment of a dryer 415 suitable as a liquid removal system. The dryer comprises a housing 416, within which are contained plural heating elements 417 and a conveyor system 418. The housing comprises an inlet 420 and an outlet 419 through which 3DP blister sheets 422, and optionally their respective support plates, are conducted by way of a conveyor. In some embodiments, the dryer comprises one or more covers 421 for the inlet and/or outlet. The dryer optionally comprises an exhaust system 423 to remove vapor and/or a heated air source 424 that provides heated air to the dryer.

Figure 45:
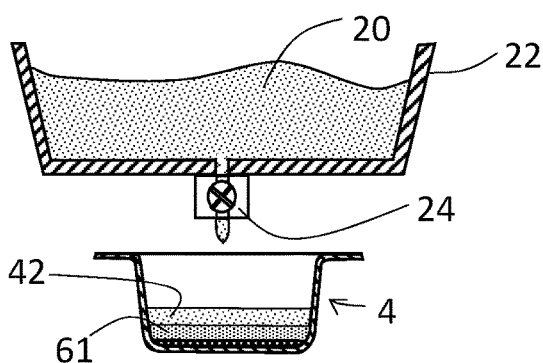
FIG. 45 illustrates depositing a powder material into the depression to form a second substantially uniform powder layer over a first bound powder layer.
Figure 46:
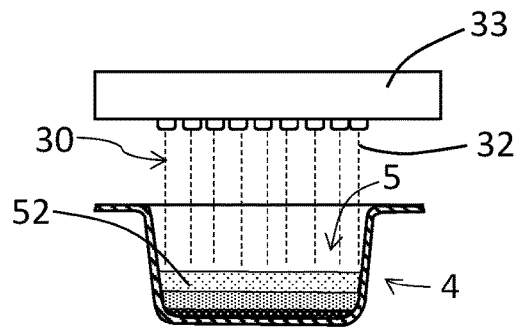
FIG. 46 illustrates applying the binding liquid onto the second substantially uniform layer of powder to form a second wetted powder layer.
Figure 47:
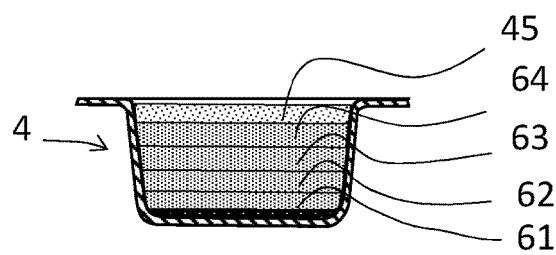
FIG. 47 illustrates forming an uppermost substantially uniform layer of powder over the previously deposited, wetted, and dried incremental bound layers of powder.
Figure 48:
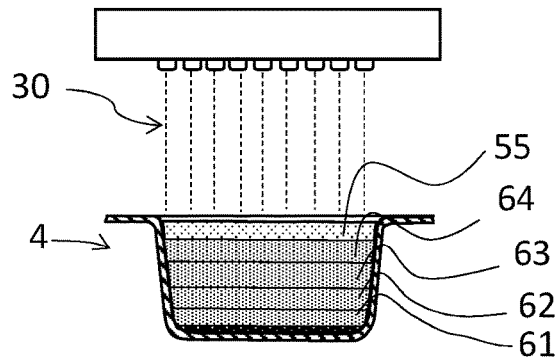
FIG. 48 illustrates applying a binding liquid onto the uppermost substantially uniform layer of powder to form an uppermost wetted powder layer.

FIGS. 45 through 49 show the deposition of additional predetermined amounts of powder 20 that are deposited as or formed into substantially uniform layers of powder. FIG. 45 shows a second substantially uniform layer 42 of powder disposed over a first bound powder layer 61 within the depression 4, while FIG. 47 shows a fifth substantially uniform layer 45 of powder deposited over four previous formed, bound powder layers 61, 62, 63 and 64. Droplets 30 or a stream of the binding liquid are deposited onto the powder layers, to form additional wetted powder layers, including a second wetted powder layer 52 shown in FIG. 46, and a fifth wetted powder layer 55 disposed over the four previous formed, bound powder layers 61, 62, 63 and 64, shown in FIG. 48.

Figure 49:
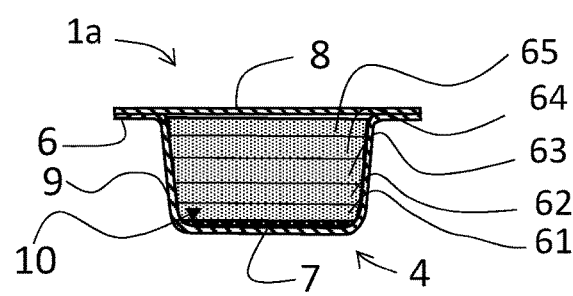
FIG. 49 illustrates the uppermost wetted powder layer having been dried to an uppermost bound layer, and a lidding sheet having been applied and sealed over the finished dosing form within the depression.

After each successive wetted powder layer is formed within the depression, any excess solvent from the binding liquid can be removed from the wetted powder layer or layers, as described above. FIG. 49 shows a fifth, uppermost bound powder layer 65 after the excess solvent has been removed from the uppermost wetted powder layer 55. Once the finished dosage form 10 has been printed, the dosage form is covered with a lidding sheet 8 and sealed into the depression 4 of the packaging to form a dosage blister 1a, also shown in FIG. 49.

In some embodiments, some or all of the wetted powder layers can be formed in sequence, and a single drying step can be performed upon the some or all wetted powder layers for solvent removal. In certain embodiments, the removal of excess solvent may be performed continuously or concurrently during materials deposition.

In FIG. 49, the finished dosage form, comprising a bound-powder matrix 10 consisting of the five bound-powder layers 61-65, has a shape and a size that substantially conforms to the interior space of the depression 4.

In an embodiment of the invention, the inner surface of the packaging sheet 6 forming the depression 4 can include a release agent. The release agent provides a means for the outer wall 11 and the bottom surface 12 of the dosage form 10 (see FIG. 1), which confront the inner surface of the wall 9 and closed end 7 of the depression 4, respectively, to easily release the dosage form 10 from, or avoid its adhering to, such inner surfaces. The release agent can be a compound that is applied to the inner surface of the depression prior to the dosage printing. A non-limiting example is a coating of Teflon® which releases the dosage form without residual compound remaining on the depression 4. The release agent can also be a compound, an inherent property or applied feature of, the plastic material of the package sheet 6, such as a plastic film laminated to the inner surface of the sheet having adhesion resistance.

In certain embodiments, the release agent may be characterized by low surface energy when compared to the surface tension of the depositing liquid, thereby limiting or mediating the extent of wetting on the inner surface of the depression, and inhibiting migration of the binding liquid along the periphery of the dosage form.

In some embodiments, for depositing a binding liquid having a surface tension in the range of 40 to 50 mN/m, the interior surface of the depression desirably has a surface energy less than 40 mN/m, and more particularly less than 35 mN/m. In some embodiments, for depositing a binding liquid having a surface tension in the range of 30 to 40 mN/m, the interior surface of the depression desirably has a surface energy 29 mN/m or less, and more particularly less than 25 mN/m. If a multilaminate cavity material is used, for example a polyvinyl chloride/polychlorotrifluoroethylene (PVC/PCTrFE) is chosen, the PCTrFE lamina (30.9 mN/m) is desirably placed on the interior surface of the depression, and the PVC lamina (41.5 mN/m) on the exterior of the depression.

In general, the surface energy of the release agent (or plastic) is desirably lower than the surface tension of the depositing fluid by 1 mN/m to 5 mN/m, or 5 mN/m to 10 mN/m, or 10 mN/m or more. Table 1 shows provides a listing of common polymers and data on their solid surface energy (source: http://surface-tension.de/solid-surface-energy.htm).

If the release agent is a further material applied to the packaging sheet that forms the depression, when employing a water-based binding liquid, the release agent is suitable for consumption and can be selected from the group consisting of an oil, wax, or fatty acid, metallic salt of fatty acid, or fatty acid ester. A suitable release agent can be selected from the materials listed in relevant compendia such as USP/NF, in excipient guides, in listings of materials that are GRAS (Generally Recognized As Safe), or in food additive regulations. Example release agents may include, without limitation, magnesium stearate, stearic acid, glyceryl dipalmitostearate, glyceryl distearate, glycerol palmitostearate, glyceryl dibehenate, mono and diglyceride mixture, glycerol monostearate, beeswax, carrnuba wax, cetyl esters wax, or combinations thereof.

While the forming of a single dosage form 10 within a single depression 4 has been illustrated, the methods and devices described herein can be used to form a plurality of dosage forms within respective depressions of a packaging material, such as a blister sheet as shown in FIG. 1. An array of blister-type depressions can include any arrangement or pattern of depressions 4, as is well known in the art.

TABLE 1

Solid surface energy data (SFE) for common polymers

| Polymer Name | CAS No. | SFE at 20° C. in mN/m | Temp. coef. SFE in mN/(m K) | Dispersive contrib. of | Polar contrib. of SFE in |
|---|---|---|---|---|---|
| Polyethylene-linear PE | 9002-88-4 | 35.7 | −0.057 | 35.7 | 0 |
| Polyethylene-branched PE | 9002-88-4 | 35.3 | −0.067 | 35.3 | 0 |

TABLE 1-continued

Solid surface energy data (SFE) for common polymers

| Polymer Name | CAS No. | SFE at 20° C. in mN/m | Temp. coef. SFE in mN/(m K) | Dispersive contrib. of | Polar contrib. of SFE in |
|---|---|---|---|---|---|
| Polypropylene-isotactic PP | 25085-53-4 | 30.1 | −0.058 | 30.1 | 0 |
| Polyisobutylene PIB | 9003-27-4 | 33.6 | −0.064 | 33.6 | 0 |
| Polystyrene PS | 9003-53-6 | 40.7 | −0.072 | −34.5 | −6.1 |
| Poly-a-methyl styrene PMS (Polyvinyltoluene PVT) | 9017-21-4 | 39 | −0.058 | −35 | −4 |
| Polyvinyl fluoride PVF | 24981-14-4 | 36.7 | — | −31.2 | −5.5 |
| Polyvinylidene fluoride PVDF | 24937-79-9 | 30.3 | — | −23.3 | −7 |
| Polytrifluoroethylene P3FEt/PTrFE | 24980-67-4 | 23.9 | — | 19.8 | 4.1 |
| Polytetrafluoroethylene PTFE (Teflon ™) | 9002-84-0 | 20 | −0.058 | 18.4 | 1.6 |
| Polyvinylchloride PVC | 9002-86-2 | 41.5 | — | −39.5 | −2 |
| Polyvinylidene chloride PVDC | 9002-85-1 | 45 | — | −40.5 | −4.5 |
| Polychlorotrifluoroethylene PCTtFE | 25101-45-5 | 30.9 | −0.067 | 22.3 | 8.6 |
| Polyvinylacetate PVA | 9003-20-7 | 36.5 | −0.066 | 25.1 | 11.4 |
| Polymethylacrylate (Polymethacrylic acid) PMAA | 25087-26-7 | 41 | −0.077 | 29.7 | 10.3 |
| Polyethylacrylate PEA | 9003-32-1 | 37 | −0.077 | 30.7 | 6.3 |
| Polymethylmethacrylate PMMA | 87210-32-0 | 41.1 | −0.076 | 29.6 | 11.5 |
| Polyethylmethacrylate PEMA | 9003-42-3 | 35.9 | −0.07 | 26.9 | 9 |
| Polybutylmethacrylate PBMA | 25608-33-7 | 31.2 | −0.059 | 26.2 | 5 |
| Polyisobutylmethacrylate PIBMA | 9011-15-8 | 30.9 | −0.06 | 26.6 | 4.3 |
| Poly(tert-butylmethacrylate) PtBMA | 25189-00-8 | 30.4 | −0.059 | 26.7 | 3.7 |
| Polyhexylmethacrylate PHMA | 25087-17-6 | 30 | −0.062 | −27 | −3 |
| Polyethyleneoxide PEO | 25322-68-3 | 42.9 | −0.076 | 30.9 | 12 |
| Polytetramethylene oxide PTME (Polytetrahydrofurane | 25190-06-1 | 31.9 | −0.061 | 27.4 | 4.5 |
| Polyethyleneterephthalate PET | 25038-59-9 | 44.6 | −0.065 | −35.6 | −9 |
| Polyamide-6,6 PA-66 | 32131-17-2 | 46.5 | −0.065 | −32.5 | −14 |
| Polyamide-12 PA-12 | 24937-16-4 | 40.7 | — | 35.9 | 4.9 |
| Polydimethylsiloxane PDMS | 9016-00-6 | 19.8 | −0.048 | 19 | 0.8 |
| Polycarbonate PC | 24936-68-3 | 34.2 | −0.04 | 27.7 | 6.5 |
| Polyetheretherketone PEEK | 31694-16-13 | 42.1 | — | 36.2 | 5.9 |

Figure 50:
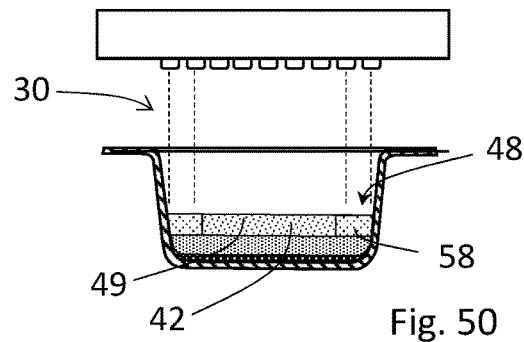
FIG. 50 illustrates an alternative embodiment wherein the binding liquid is applied only at the peripheral portions of the second substantially uniform layer of powder, leaving a central portion of unwetted/unbound powder.
Figure 51:
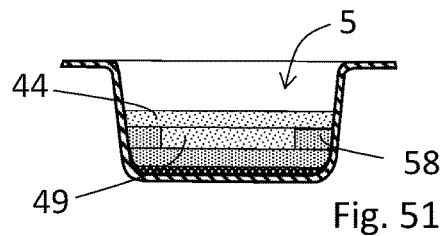
FIG. 51 illustrates applying a third substantial uniform layer of powder upon the second layer having the central portion of unwetted and unbound powder illustrated in FIG. 50.
Figure 52:
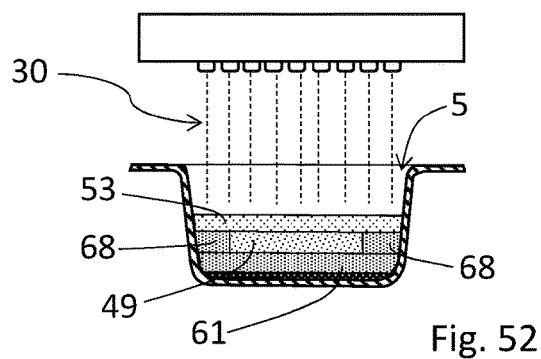
FIG. 52 illustrates applying a binding liquid upon the third substantially uniform layer of powder to form a third wetted powder layer, over the second layer having the central portion of unwetted and unbound powder.
Figure 53:
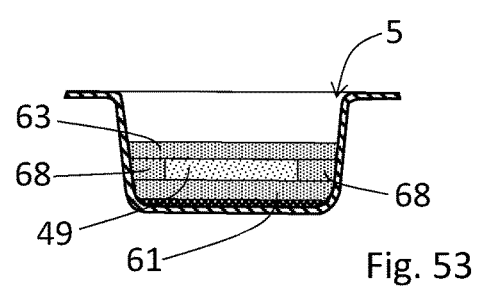
FIG. 53 illustrates the third uppermost wetted powder layer having been dried to a third bound layer.

In another embodiment, as illustrated in FIGS. 50-53, the print head and nozzles of the 3D printing assembly can be configured to apply droplets 30 of binding liquid upon any specific portion of a substantially uniform layer of powder. In FIG. 50, the binding liquid is applied only at the side portions 48 of a second (or subsequent, or any) layer 42 of powder material, to form a peripheral portion of wetted powder 58 and leaving a central portion 71 of unwetted, unbound powder. After drying of the wetted powder 58 to a peripheral portion of bound powder 68, an additional powder layer can be applied. FIG. 51 illustrates applying a third powder layer 43 upon the layer below whose side portions 58 comprise bound powder material, but whose central portion 49 of powder does not have any binding liquid. As illustrated in FIG. 52, droplets 30 of binding liquid are deposited to the third powder layer 43, forming a wetted powder layer 53, without applying such a significant amount of liquid that could penetrate down through and into the central portion 49 of unwetted, unbound powder in the second layer 42 of powder material. In such an embodiment, the portions of bound powder in the peripheral portion 68 of the second bound powder layer 62, and/or a wetted (or bound) powder layer 63 there-above and the first bound powder layer 61 there-below, shown in FIG. 53, provide a resilient structure sufficient to contain a powder-only volume, such as central portion 49 of powder, while maintaining the structural integrity of the resulting dosage form 10.

Figure 57:
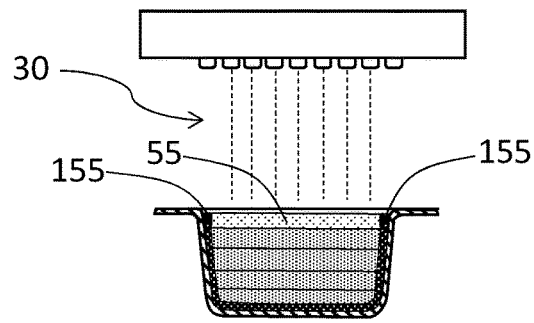
FIG. 57 illustrates applying the binding liquid upon the top portion of the uppermost substantially uniform powder layer to form an uppermost wetted powder layer with a peripheral outer coating.
Figure 58:
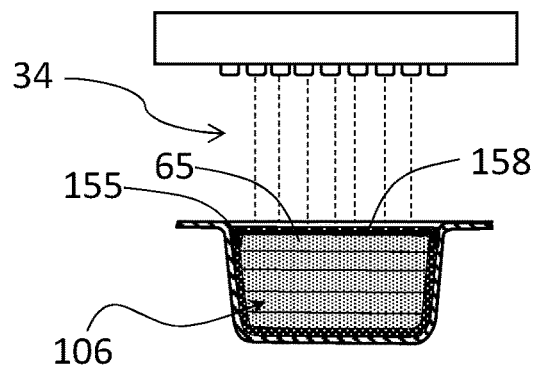
FIG. 58 illustrates the uppermost wetted powder layer having been dried to an uppermost bound layer, and applying the binding liquid upon the top portion of the uppermost powder layer to form a wetted coating.
Figure 59:
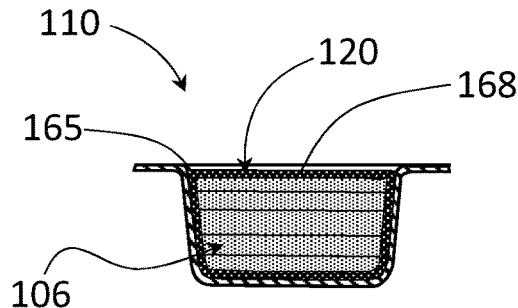
FIG. 59 illustrates the finished dosage form, after drying or curing the wetted coating on the top portion of the uppermost powder layer, to form an outer coating that surrounds the incremental bound powder layers.

FIGS. 54-59 show an alternative embodiment of the method of forming a dosage form, within a depression 4 of the blister-type packaging 1, comprising a shaped bound-powder core 106 having a hard and resilient binder coating 120 that surrounds the core 106 as shown in FIG. 59.

Figure 54:
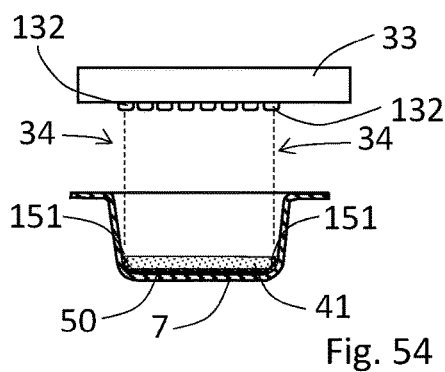
FIG. 54 illustrates an alternative embodiment wherein a binding liquid is applied only at the peripheral portions of the first layer of powder, to form an outer coating at a peripheral or edge portion of the first layer of powder.

FIG. 54 illustrates a first uniform layer 41 of powder material deposited into a depression 4, over a lower coating of binder liquid at the closed end of the interior space 5 of the depression 4, thereby forming a base layer 50 of wetted powder covering the inside surface of the closed end 7, and the remaining portion of the powder layer 41 above. Selected nozzles 132 of the 3D printing assembly 33 are configured to apply droplets or a stream 34 of a binding liquid selectively at the peripheral edges of the first powder layer 41, thereby wetting the powder at the peripheral edges of the powder layer 41 to form a wetted peripheral coating 151. In the illustrated embodiment, a central portion of the powder layer 41 is not wetted with the droplets 34 of the second binding liquid. The second binding liquid can be same as the aforementioned binding liquid for wetting the uniform layers of powder, or can be different. Typically, the concentration of second binding liquid applied at the peripheral portions 151 is greater than that applied for wetting the powder layers. In one embodiment, the quantity of the binding liquid is sufficient to coat and cover substantially all of the particles of powder to form a liquid-continuous wetted powder.

In one embodiment, the droplets 34 are applied using an inkjet printing system 33 in which a multiplicity of printing nozzles 132 are aligned in an array, typically one or more linear rows of nozzles 132. The depression 4 containing the powder layer 41 and the array of nozzles 132 are moved with respect to one another, the depression 4 passing horizontally beneath the array of nozzles 132 while the droplets 34 are deposited in a timed, predetermined pattern so that the droplets 34 of the binding liquid are only applied at the peripheral portions of the powder layer 41. In one embodiment, the array of nozzles 132 are stationary, and the depression or depressions 4 are moved horizontally and below the nozzles 132. In an alternative embodiment, the depression 4 is stationary, and the array of nozzles 132 are passed horizontally over the depression 4. As the depression 4 is passing below the array of nozzles 132, selected ones of the nozzles along the array 33 are activated to express droplets 34 only as the corresponding portions of the powder layer 41 pass below, the resulting expression of droplets 34 forming an annular pattern of liquid binder 151 over the peripheral portions of the powder layer 41.

In another embodiment, not shown, the droplets 34 are applied from a liquid spray nozzle in a fixed and uniform pattern while the depression 4 containing the powder layer 41 is disposed beneath the nozzle. The depression(s) 4 and the nozzle(s) are typically both stationary, although in an alternative embodiment they can both be moving simultaneously and synchronously. In a typical embodiment, the nozzle emits an annular pattern of droplets as a hollow cone.

In another embodiment, the droplets 34 are applied using a liquid streaming nozzle, which is configured to deposit a volume of the second binding liquid without the precise droplet size control of an inkjet nozzle. Typically, the spray velocity of the droplets of such liquid streaming nozzles are significantly slower than that of the inkjet spraying system. A non-limiting example of a liquid streaming nozzle is an ultrasonic deposition nozzle, available as the AccuMist™ System from Sonotek Corporation, Milton N.Y. These spray nozzles result in low velocity droplets, which causes less disturbance to powder materials, with minimal overspray and a wide range of volumetric rates and median droplet size (diameter). The spray patterns are available in a variety of patterns, including both wide and narrow conical patterns, and focused linear streams.

Figure 55:
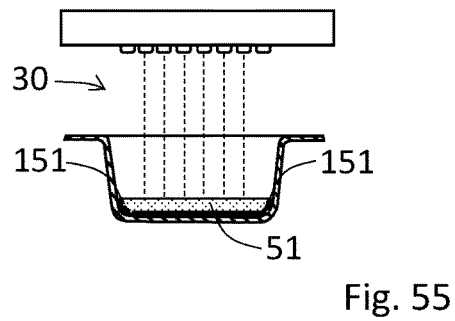
FIG. 55 illustrates applying the binding liquid upon a central portion of the first layer of powder to form a first wetted powder portion surrounded by the coating at the peripheral or edge portion of the first layer of powder.

FIG. 55 illustrates applying droplets 30 of a first binding liquid as described above to a central portion of the first powder layer 41, thereby forming a first wetted powder layer 51. The wetted peripheral portion 151 typically surrounds and envelopes the central wetted portion of the wetted powder layer 51. In some embodiments, the order of applying the binding liquids can be reversed, by first applying the binding liquid to the central portion of the powder layer 41 to form the wetted powder portion, followed by applying the second binding liquid to form the wetted peripheral portion 151.

Figure 56:
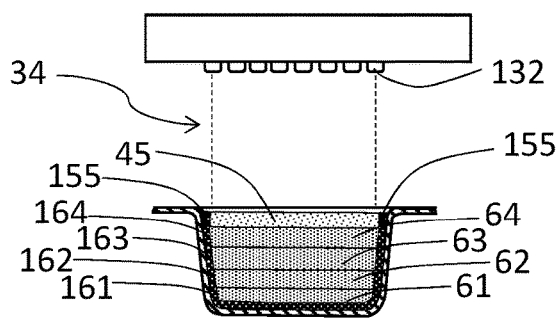
FIG. 56 illustrates applying the binding liquid at the peripheral portions of an uppermost, substantially uniform powder layer, to form an outer coating at a peripheral or edge portion of the uppermost layer of powder.

Once dried, the wetted peripheral portion 151 is formed into a stable solidified or resilient peripheral coating portion 161, with a bound powdered layer portion 61 within, as shown in FIG. 56. The cycle is repeated to deposit three additional uniform powders, each of which is wetted with droplets or a stream 34 of the second binding liquid at the peripheral edges of the respective second, third and fourth powder layers, and wetted within the respective central portions of the powder layers to form wetted powder layers. Each layer can be processed separately, or in groups of two or more layers, to remove excess binder solvent, and thereby form the second, third and fourth bound powder layers 62, 63 and 64, having respectively the solidified or resilient peripheral coating portions 162, 163 and 164, shown in FIG. 56. Also as shown in FIG. 56, after a fifth uniform powder layer 45 is deposited, selected nozzles 132 of the 3D printing assembly 33 are configured to apply droplets or a stream 34 of the second binding liquid at the peripheral edges of the fifth, uppermost powder layer 45, wetting the powder at the peripheral edges, to form a wetted peripheral coating 155. In FIG. 57, the remaining portion of the uppermost uniform powder layer 45 is contacted with droplets 30 of the first binding solution, to form a central portion of wetted powder layer 55 with the wetted peripheral coating 155.

In an alternative embodiment, the wetted peripheral coating 155 can first be processed to remove excess binder solvent from the wetted peripheral coating 155 and form a solidified or resilient peripheral coating portions 165, prior to wetting the remaining unwetted portion of the fifth uniform powder layer 45 with binding liquid.

As shown in FIG. 58, droplets or a stream 34 of the second binding liquid are deposited onto the top, central portion of the uppermost, fifth powder layer 55, contacting and overlapping the solidified or resilient peripheral coating portions 165, and forming a wetted coating 158. FIG. 59 illustrates then the finished dosage form 110, after drying or curing the wetted coating 158 on the top portion of the uppermost bound powder layer 65, having a top resilient coating 168 that completes the forming of an outer coating 120 that surrounds the shaped, bound dosage core 106.

Figure 60:
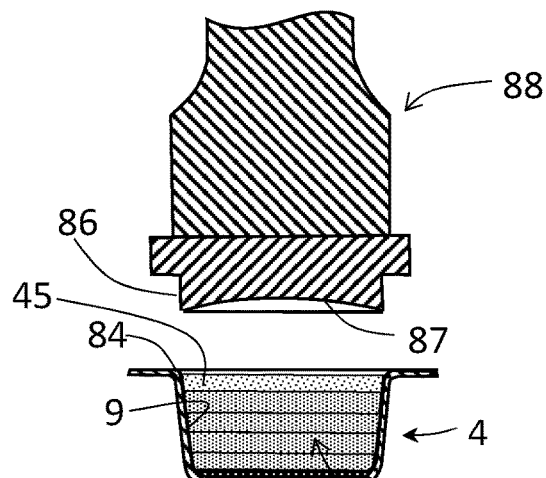
FIG. 60 illustrates a tamper having a concave-shaped bottom surface, positioned above a top layer of the powder material in a depression.
Figure 61:
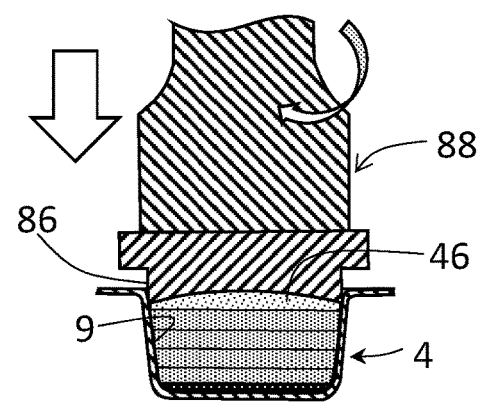
FIG. 61 illustrates the tamper positioned into the depression, and pressing down on the upper surface of the powder layer.
Figure 62:
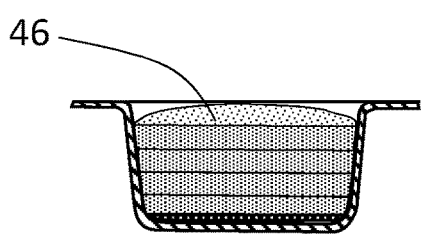
FIG. 62 illustrates the convex upper surface of the uppermost powder layer, shaped by the tamper.

In another embodiment, FIG. 60 illustrates a sectional view of a tamper 88, having an under surface 87 that defines a cavity and a corresponding rim 89, poised to register onto the top layer 45 of the powder material in the depression 4. The cross-sectional shape of the tamper 88, and hence the shape of the under surface 87 of the cavity, is configured to match that of the desired dosage form being made. Non-limiting examples of a tamper are described in International Publication WO2017/034951, the disclosure of which is incorporated by reference in its entirety. In the illustrated embodiment, the cavity shape is a concave circle, but in other embodiments can be a concave oval, square rectangular, or any other geometrical shape. The rim 89 is configured to register within the inside walls 9 of the depression 4, as shown in FIG. 61, when placed against the upper surface of the top powder layer 45 as shown by the arrow, forming the upper surface of the shaped top powder layer 46 into a corresponding convex counter-shape, as shown in FIG. 62. The tamper 88 can be lowered (down arrow, FIG. 61) onto the loose, deposited powder to smooth, contour, or modify its surface. In some embodiments, the tamper 88 is lowered once and raised, or can be lowered two or more times to the same or a different depth to effect one or a series of tamping steps. In some embodiment, the tamper can be lowered into contact with the powder and advanced downward based on a linear (vertical) distance of travel, the extent of linear distance traveled effecting the degree of tamping and/or leveling of the deposited powder layer.

The level or extent of tamping can effect an increase in the areal density of the powder material or wetted powder material. In some embodiments, the density of a powder material can be increased by tamping the powder material, by up to about 33%. In some embodiments, the increase in density effected by tamping of the powder material is up to about 30%, or up to about 25%, or up to about 20%, and can be at least about 5%, or at least about 10%, or at least about 15%, or at least about 20%. The desired or actual increase in density can be varied, or selected, based on the composition of the powder material, and/or the portion of the dosage form which the tampered powder material forms. In some embodiments, tamping can increase the density of a deposited layer of powder material of at least 0.05 grams per cubic centimeter (g/cc), including at least 1.0 g/cc, and up to about 1.5 g./cc, including up to about 1.0 g./cc. In some embodiments, tamping can increase the density of a wetted powder material of at least 0.03 grams per cubic centimeter (g/cc), including at least 0.05 g/cc, of at least 1.0 g/cc, and up to about 1.5 g/cc, including up to about 1.0 g/cc.

Figure 63:
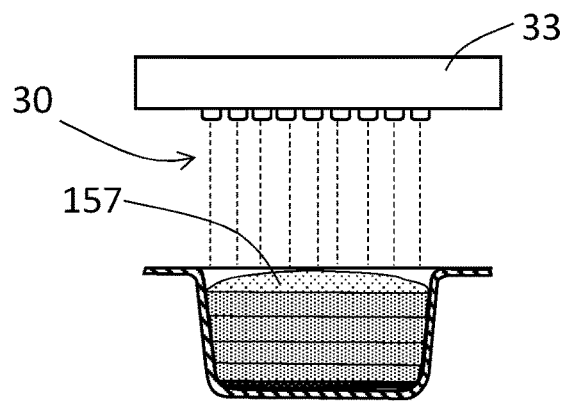
FIG. 63 illustrates depositing a binding liquid onto the convex-shaped powder material to form the last, shaped wetted powder layer.

In some embodiments, the tamper can be lowered into contact with the powder and advanced based on a detected or measured linear force or pressure on the tamper, the extent of linear force or pressure effecting the degree of tamping and/or leveling of the deposited powder layer. In some embodiments, the tamper 88 is rotated, as illustrated in FIG. 61, in one rotational direction, as the tamper is being lowered. The rotation of the tamper 88 while lowering improves the uniformity of depth of the powder layer, and the uniformity of areal tamping of the powder. The movement of the tamper 88 can be controlled by any control system known in the art. As illustrated in FIG. 63, after the tampers 88 is raised, the depression 4 containing the bound powder layers and the shaped top powder layer 46 can be moved to a printing region, where binding liquid can be applied onto the convex-shaped powder material layer 46 to form the last, uppermost bound powder layer 157.

Though the under surface of the tampers 88 that contacts the in-process 3DP article is depicted as being a concave, circular shape, the under surface of a tamper can be a flat or other non-flat shape, meaning shaped (or contoured) as desired.

Figure 64:
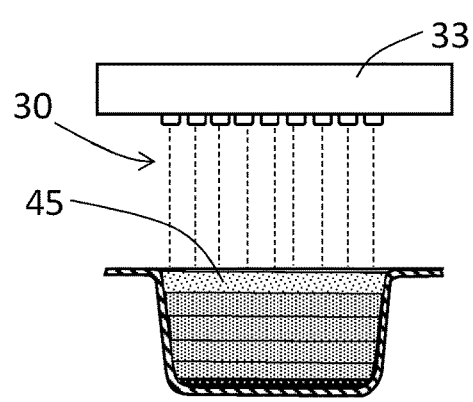
FIG. 64 illustrates the wetting an uppermost powder layer to form an uppermost wetted powder layer.
Figure 65:
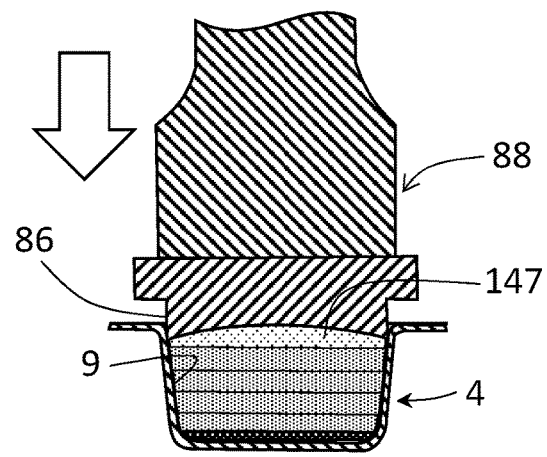
FIG. 65 illustrates a tamper used to shape the uppermost wetted powder layer of FIG. 64.

In an alternative embodiment, illustrated in FIGS. 64 and 65, a tamper can be used to shape an uppermost wetted powder layer. After a fifth uniform powder layer 45 is deposited, selected nozzles of the 3D printing assembly 33 are configured to apply droplets 30 of the binding liquid onto the fifth, uppermost powder layer 45, wetting the powder to form an uppermost wetted powder layer 46, as shown in FIG. 64. In some embodiments, the uppermost wetted powder layer 46 can be shaped, tamped or marked, using a tamper. A tamper 88 can be lowered and placed against the upper surface of the uppermost wetted powder layer 46 as shown by the arrow, to form the uppermost bound powder layer 157, as shown in FIG. 65.

In some embodiments, the tamper and tamper system can be used to form a one or more, such as a series, tamped powder layers, or tamped wetted powder layers, within a depression. The one or more tamped powder layers can be uniformly or non-uniform tamped, resulting in one or more uniformly or non-uniform densified powder layers, or in one or more uniformly or non-uniform densified wetted powder layers.

In some embodiments, a tamper of one type or shape can be used on one or more powder layers or wetted powder layers, and a second tamper of a different type or shape can be used on a different one or more powder layer or wetted powder layer, to provide different aesthetic or performance effects or properties to the resulting dosage form.

In some embodiments, a rotary tamping device can comprise a laterally-extending cylindrical outer surface with a pattern of tampers extending radially outwardly from the cylindrical surface. The positioning of the tampers can be moved axially to adjust the distance that each tamper extends from the outer surface, to allow the tamper to extend different distance down into the depression.

Figure 66:
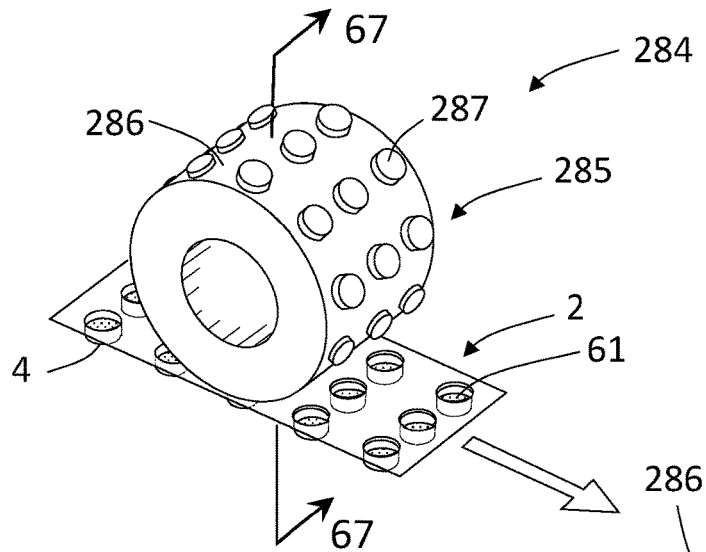
FIG. 66 illustrates a rotary tamping apparatus having tampers for tamping the powder layer in a pattern of depressions of a blister sheet.
Figure 67:
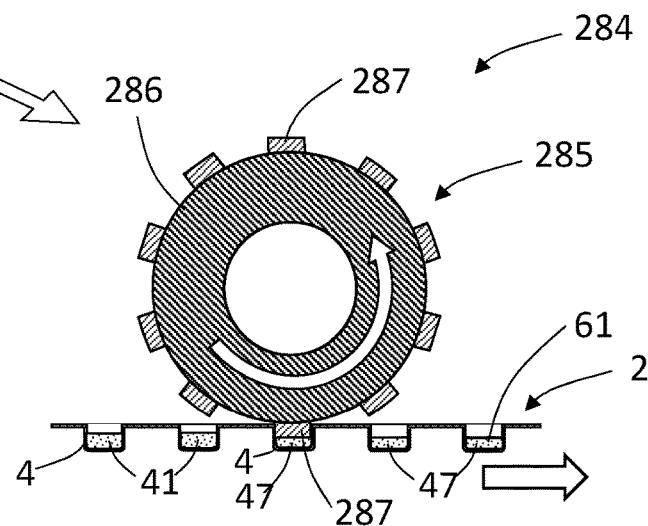
FIG. 67 shows an elevation sectional view through the rotary tamping apparatus and blister sheet of FIG. 66.

An automated tamping apparatus can be provided for tamping a plurality of dispensed powder layers within depressions. An example is a rotary tamping apparatus shown in FIG. 66, illustrated in sectional view over a blister sheet 2 in FIG. 67. The rotary tamping apparatus 284 includes a rotary drum 285 having an outer surface 286 in which are disposed a plurality of tampers 287 in a number sufficient to tamp each of the number of depressions 4 in the blister sheet 2. The blister sheet 2 with a desired number of depressions 4 is moved (lateral arrow) beneath the rotary tamping apparatus, in synchronous speed with the rotation of the rotary drum 285 with the tampers 287 in registry with the depressions 4. The tamper is sufficiently sized and shaped to extend into each depression to tamp a layer of powder material 41 within each depression 4, forming a tamped powder layer 47.

Other tamper faces of various sizes, shapes and contours are contemplated. A tamper face may comprise raised (or potentially recessed) lettering, numbering, or other symbols in order to provide an imprint into an exterior or interior incremental layer of a 3DP article that reflects the contour of the tamper face in reverse (i.e., a raised feature on the tamper face creating a lowered feature on the incremental layer, and vice versa). The tamper face may include specific patterns or textures with a similar goal of creating and imprint into an interior or exterior incremental layer of a 3DP article. In certain embodiments, the pattern or texture of features on the tamper face allows the powder from more than one incremental layer to mingle within the same horizontal slice of a 3DP article. For example, in a case for which there are two sequential incremental layers with different respective powders, instead of each powder substantially remaining within its own respective layer, one or both powders may shift upward or downward into a neighboring incremental layer when displaced by the action of a non-smooth tamper face having raised or recessed features. In certain embodiments, this may include depressions that are created in an instant incremental layer comprised of a first powder that is subsequently filled with a second powder on the next powder spreading step, or this may include raised areas in an instant incremental layer comprised of a first powder and extending into the space allocated for the next incremental layer having a second respective powder, or combinations of both.

In some embodiments, a tamper system consists of a pattern of tampers, positioned in registry over a corresponding pattern of depressions. In some embodiments, the pattern of tampers moves in a vertical direction, orthogonally to the base of the depressions. In some embodiments, the pattern of tampers moves in unison, as an assembly, though in some embodiments each tamper moves independent of other tampers. In some embodiments, the pattern of tampers is fixed in lateral position, and registration with the pattern of depressions is provided by maneuvering the pattern of depressions (for example, a blister-type packaging sheet having a pattern of depressions 4). In some embodiments, the pattern of depressions is fixed in lateral position, and registration with the pattern of tampers is provided by maneuvering the pattern of tampers. In some embodiments, both the pattern of tampers and the pattern of depressions can be maneuvered independently into registry with the other.

Generally, a 3DP equipment assembly and/or apparatus can comprise various subsystems including one or more three-dimensional printing build systems, and optionally one or more liquid removal systems. The system can comprise one or more three-dimensional printing build systems, one or more liquid removal (drying) systems and optionally one or more other systems. In some embodiments, the equipment assembly can comprise one or more (sub)systems selected from the group consisting of one or more upper tamper systems, one or more control systems, and one or more inspection systems. For example, in certain embodiments of a depression 3DP system, it is not necessary to have a harvesting system since substantially all of the powder material entering a depression is incorporated into a respective dosage form within the depression. Similarly, in certain embodiments of a depression 3DP system, it is not necessary to eject the formed tablets, transport them, and/or feed them into separate packaging, since the tablets are forming in situ in the packaging.

Figure 68:
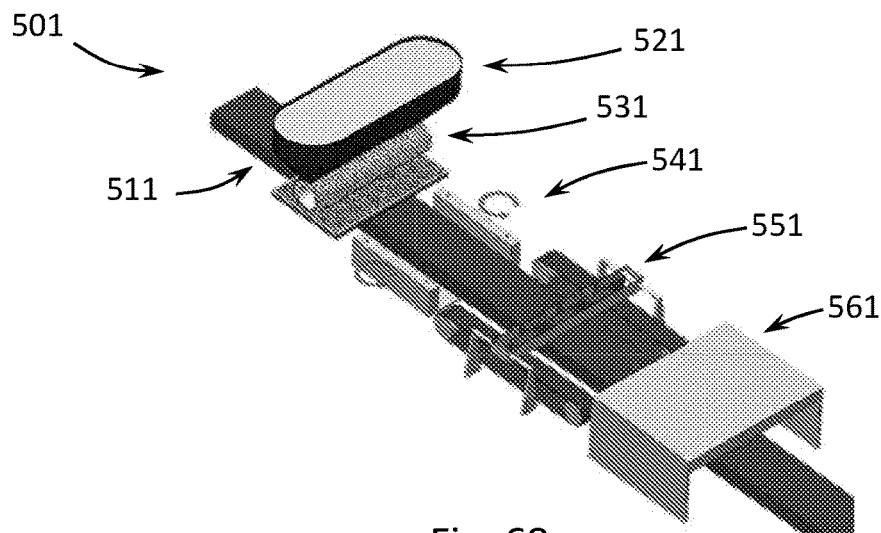
FIG. 68 illustrates a linear 3DP equipment assembly that includes a powder bin and rotary dosing apparatus, a powder leveling device, a printing device, and a drying apparatus.

FIG. 68 illustrates a first, non-limiting embodiment of a 3DP equipment assembly, consisting of a linear equipment assembly 501. A conveyor system 511 in configured to move a blister sheet, typically supported upon a support plate. Non-limiting examples of a conveyor are described in US Publication 2014/0065194 (Aprecia Pharmaceuticals Company), the disclosure of which is incorporated by reference in its entirety, wherein a build module as described therein can comprise a support plate or a module for transporting a support plate, having one or more blister sheets supported thereon.

The equipment assembly 501 includes a powder bin 521 and rotary dosing apparatus 531, as described herein, or other embodiment disclosed herein for dispensing powder material into the depressions. The equipment assembly 501 includes a leveling device or apparatus 541, illustrated as vibratory plate, or other embodiment of a powder leveling means, device or apparatus described herein. The equipment assembly 501 includes a printing device or apparatus 551, such as an inkjet printing system as described herein. The equipment assembly 501 includes a drying apparatus 561, illustrate as an irradiative heating apparatus, or other embodiment of a drying apparatus as described herein.

Figure 69:
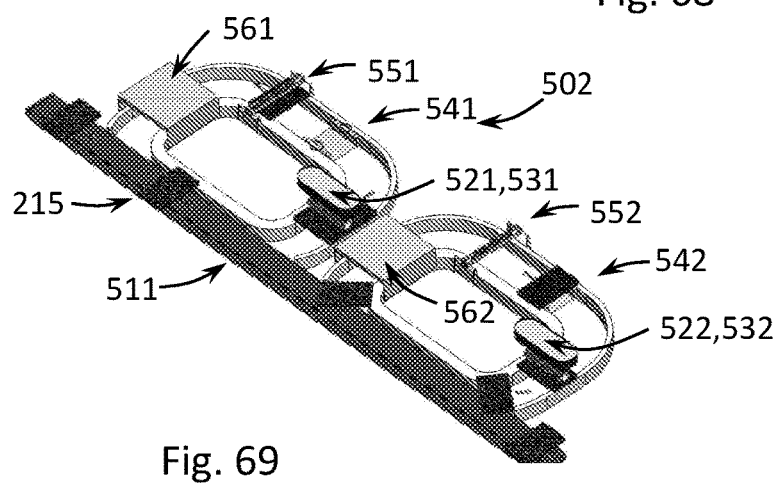
FIG. 69 illustrates a 3DP equipment assembly having two assemblies in series, each arranged in a continuous loop including a powder bin and rotary dosing apparatus, a powder leveling apparatus, a printing apparatus, and a drying apparatus.

FIG. 69 illustrates a second, non-limiting embodiment of a 3DP equipment assembly 502, consisting of at least two assemblies 551 and 552, arranged in series. Each of assemblies 551 and 552 are arranged in a continuous loop, onto which and from which a supported blister sheet 215 can be conducted. The assembly 551 includes a powder bin 521 and rotary dosing apparatus 531, a leveling apparatus 541, a printing apparatus 551, and a drying apparatus 561. The assembly 552 includes a powder bin 522 and rotary dosing apparatus 532, a leveling apparatus 542, a printing apparatus 552, and a drying apparatus 562. In some embodiments, a supported blister sheet 215 can be passed one or more times through the first assembly 551, or passed one or more times through the second assembly 552, or passed one or more times through both of the first assembly 551 and the second assembly 552. In some embodiments, the powder material dispensed from the powder bin 521 is different from the powder material dispensed from the powder bin 522. In some embodiments, the powder dispensing apparatus can be a different powder dispensing apparatus, and the dispensing apparatus of the first assembly 551 can be different from the dispensing apparatus of the second assembly 552. In some embodiments, the powder leveling apparatus 541 of the first assembly 551 can be different from the powder leveling apparatus 542 of the second assembly 552. In some embodiments, the binding liquid applied to the powder material from the printing apparatus 551 is different from the binding liquid applied to the powder material from the printing apparatus 552. In some embodiments, the drying apparatus 561 is different from the drying apparatus 562.

Figure 70:
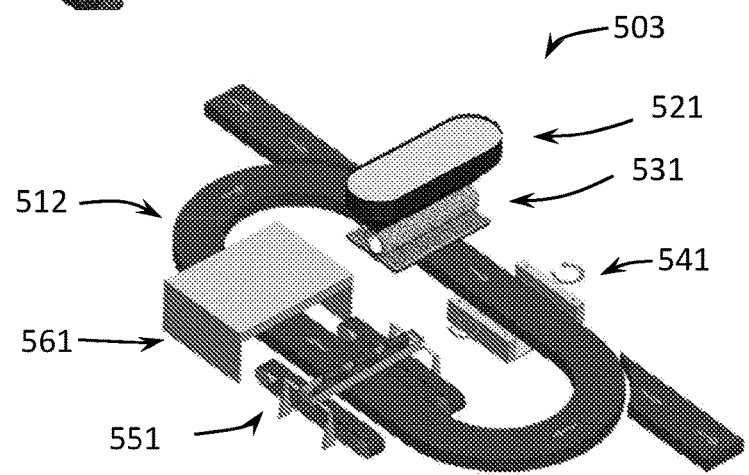
FIG. 70 illustrates a 3DP equipment assembly having a continuous loop conveyor, consisting of a powder bin and rotary dosing apparatus, a powder leveling apparatus a printing apparatus, and a drying apparatus on different portions of the looped conveyor.

FIG. 70 illustrates a third, non-limiting embodiment of a 3DP equipment assembly 503, consisting of a continuous loop 512, onto which and from which a supported blister sheet 215 can be conducted (illustrated by green arrows). The assembly 553 includes a powder bin 521 and rotary dosing apparatus 531, and a powder leveling apparatus 541 along a first portion of the looped conveyor 512, and a printing apparatus 551 and a drying apparatus 561 on a second portion of the looped conveyor 512. Supported blister sheet 215 can be brought into the system 503, and taken away from the system 503, along the first portion of the looped conveyor 512.

Figure 71:
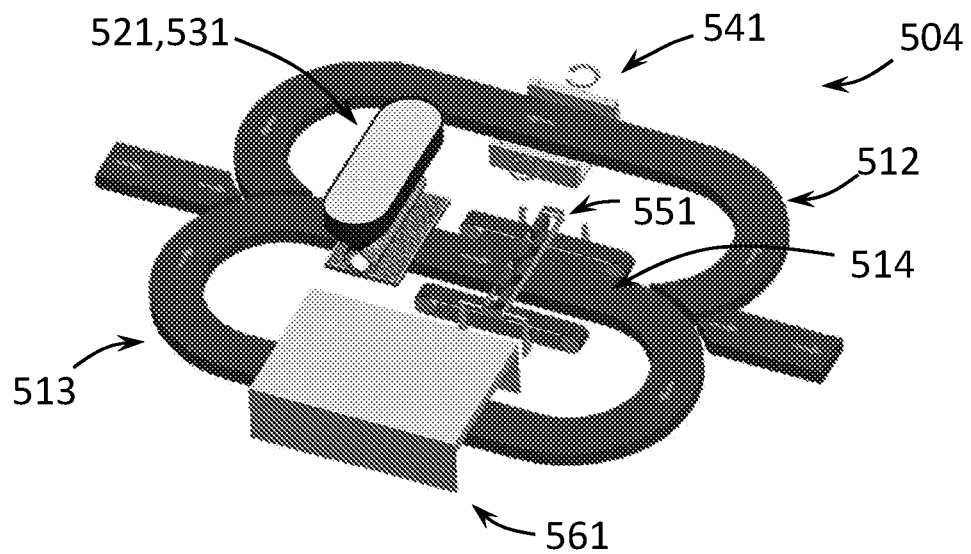
FIG. 71 illustrates a 3DP equipment assembly having a first and second continuous loop with a common conveyor portion including a powder bin and rotary dosing apparatus, and a printing apparatus. A powder leveling apparatus and a drying apparatus are positioned along the outer loops of the respective first and second continuous loops.

FIG. 71 illustrates a fourth, non-limiting embodiment of a 3DP equipment assembly 504, consisting of a first continuous loop 512, and a second continuous loop 513, with the two loops 512 and 513 sharing a common conveyor portion 514. The assembly 504 includes a powder bin 521 and rotary dosing apparatus 531, and a printing apparatus 551 along the common conveyor portion 514. After exiting the printing apparatus 551, the supported blister sheet 215 can be directed either along an outer loop the first continuous loop 512 or along an outer loop of the second continuous loop 513. A powder leveling apparatus 541 is disposed along the first continuous loop 512, and a drying apparatus 561 is disposed along the second continuous loop 513. A supported blister sheet 215 can be passed along the common conveyor portion 514 and through the powder dispensing apparatus (powder bin 521 and rotary dosing apparatus 531) and the printing apparatus 551 to form a wetted powder layer within the depressions. The operation can select to either direct the supported blister sheet 215 to the leveling apparatus 541, or to the drying apparatus 561. In some embodiments, the supported blister sheet 215 can be passed through the printing apparatus 551 without applying a binding liquid, whereby the pile of powder material deposited in the powder dispensing system is passed to the leveling system 541 along the first continuous loop 512 to level the powder material, and that passed back along the common conveyor portion 514 and through the printing apparatus 551 to form the wetted powder layer within the depressions.

Figure 72:
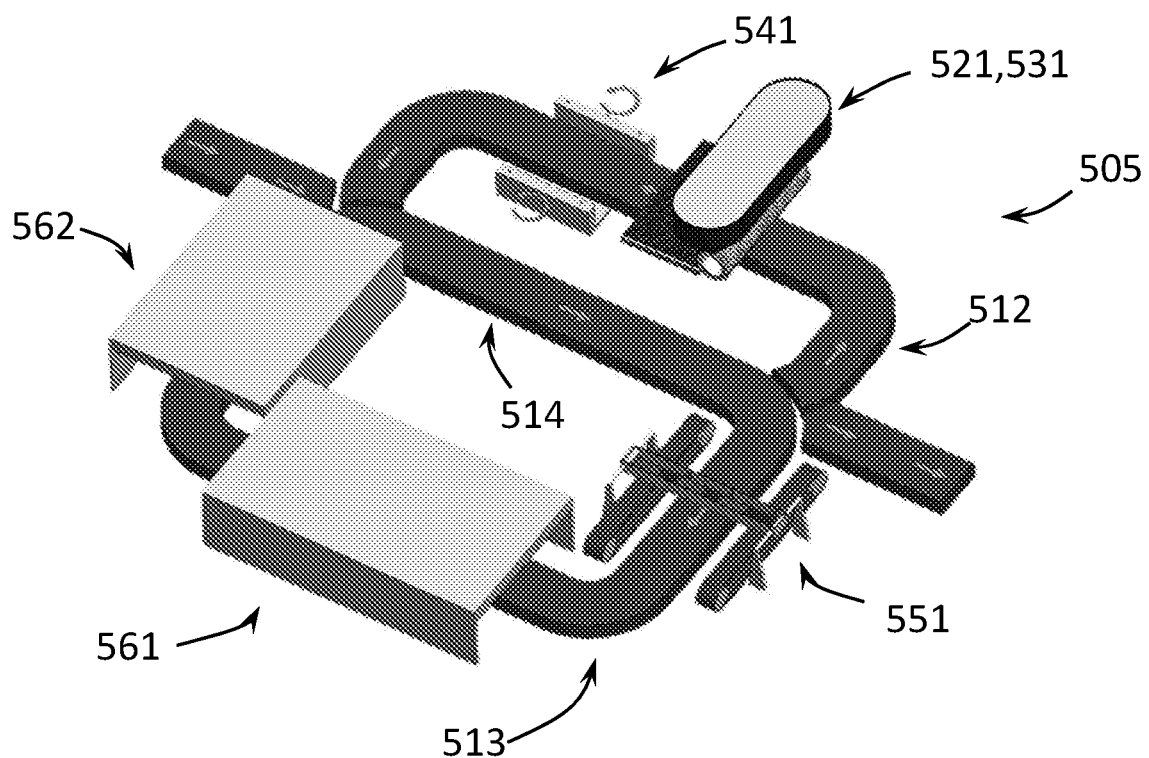
FIG. 72 illustrates a 3DP equipment assembly having a first and continuous loop, sharing a common conveyor portion. The first continuous loop includes a powder dispensing apparatus and a leveling apparatus along an outer portion, and the second continuous loop includes a printing apparatus and a pair of drying apparatus.

FIG. 72 illustrates a fifth, non-limiting embodiment of a 3DP equipment assembly 505, consisting of a first continuous loop 512, and a second continuous loop 513, with the two loops 512 and 513 sharing a common conveyor portion 514. The assembly 505 includes a powder dispensing apparatus (powder bin 521 and rotary dosing apparatus 531) and a leveling apparatus 541 along an outer portion of the looped conveyor 512, and a printing apparatus 551 and a pair of drying apparatus, consisting of a first drying apparatus 561 and a second drying apparatus 562, along an outer portion of the looped conveyor 513. The first continuous loop 512 provides for dispensing and leveling a powder material into the depressions of the supported blister sheet 215, while the second continuous loop 513 provides for dispensing of binding liquid onto the powder layers, and drying of the residual binding liquid (or the solvent therein) from the formed tablet. The first drying apparatus 561 and the second drying apparatus 562 can independently selected from any of the embodiments of a drying apparatus described herein. The first drying apparatus 561 can be different from the second drying apparatus 562.

The powder can comprise one or more materials suitable for pharmaceutical or non-pharmaceutical use. In some embodiments, the powder comprises one or more pharmaceutical excipients, one or more pharmaceutically active agents, or a combination thereof. In some embodiments, the three-dimensionally printed article is a pharmaceutical dosage form, medical device, medical implant, or other such article as described. Exemplary types of pharmaceutical excipients that can be included in a three-dimensionally printed article include, by way of example and without limitation, chelating agent, preservative, adsorbent, acidifying agent, alkalizing agent, antifoaming agent, buffering agent, colorant, electrolyte, flavorant, polishing agent, salt, stabilizer, sweetening agent, tonicity modifier, anti-adherent, binder, diluent, disintegrant, glidant, lubricant, opaquant, polishing agent, plasticizer, other pharmaceutical excipient, or a combination thereof.

One or more binders can be included in the bound-powder matrix. The binder can be included in either the powder material or in the binding liquid. The binder is independently selected upon each occurrence. Adhesion of the particles to and/or by the binder occurs either when the binder is contacted by the binding liquid from the printhead or when it is present (i.e., soluble) in the binding liquid. The binder is preferably water soluble, aqueous fluid soluble, partially water soluble or partially aqueous fluid soluble. In some embodiments, the printing fluid comprises 1-20% wt, 5-15% wt or 8-12% wt of binder. In some embodiments, the bulk powder comprises more than 0.1% to 10% wt, 5 to 15% wt, 0 to 15% wt, 8-14% wt or 9-11% wt of binder. In some embodiments, the printed matrix comprises 1-20% wt, 5-14 wt or 8-12% wt of binder. In some embodiments, binder is absent from the printing fluid or absent from the bulk material. Suitable binders include water-soluble synthetic polymer, polyvinlypyrrolidone (povidone), sorbitol, mannitiol, xylitol, lactitol, erythritol, pregelatinized starch, modified starch, hydroxypropylmethylcellulose and others. The preferred binder is polyvinylpyrrolidone, e.g. PVP K30, modified starch (e.g., starch sodium octenylsuccinate), mannitol or a combination thereof. PVP with a K value different from 30 may be used, including without limitation PVP K25 and PVP K90.

In some embodiments, the powder material comprised in each of the one or more powder layers is the same powder material compositionally. In some embodiments, the powder material in one or more powder layers is different from the powder material in another powder layer. In such embodiments, the different compositional powder materials can comprise different active pharmaceutical ingredients (APIs) or API placebos, or no API content.

Pharmaceutically active agents generally include physiologically or pharmacologically active substances that produce a systemic or localized effect or effects in animals, cells, tissue, organs, non-humans and humans.

Whenever mentioned and unless otherwise specified, the term "active agent" includes all forms of the active agent including neutral, ionic, salt, basic, acidic, natural, synthetic, diastereomeric, isomeric, enantiomerically pure, racemic, hydrate, solvate, chelate, derivative, analog, optically active, optically enriched, free base, free acid, regioisomeric, amorphous, anhydrous and/or crystalline forms.

In some embodiments, the powder material composition in a powder layer can be the same. In some embodiments, one region of a powder layer can comprise a powder material that differs compositionally from a powder comprises in another region of the powder layer.

A three-dimensionally printed dosage form can comprise one, two or more different active agents. Particular combinations of active agents can be provided. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; 4) a first drug having a first type of biological activity and a different second drug having a different second type of biological activity. Exemplary combinations of active agents are described herein.

The active agent can be independently selected at each occurrence from active agents such as an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, antidepressant agent, antidiabetic agent, antineoplastic agent, anti-psychotic agent, neuroleptic agent, antihypertensive agent, hypnotic agent, sedative agent, anxiolytic energizer agent, antiparkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, anti-ulcerant agent, antiflatulent agent, anti-incontinence agent, cardiovascular agent or a combination thereof. A description of these and other classes of useful drugs and a listing of species within each class can be found in Martindale 37$^{th}$ Edition (2017), The Extra Pharmacopoeia, 31ST Ed. (The Pharmaceutical Press, London 1996), the disclosure of which is incorporated herein by reference in its entirety.

Exemplary types of non-pharmaceutical excipients that can be included in the powder material can include, by way of example and without limitation, ash, clay, ceramic, metal, polymer, biological material, plastic, inorganic material, salt, other such materials or a combination thereof.

In some embodiments, the powder comprises one or more, two or more, three or more, four or more, five or more, six or more, seven or more, eight or more, nine or more, ten or more or plural components, each component being independently selected at each occurrence. In some embodiments, the equipment assembly comprises one or more, two or more, three or more, four or more, five or more, six or more, seven or more, eight or more, nine or more, ten or more or plural powder (or solid component) supply reservoirs.

The binding liquid applied to the powder can be a solution or suspension. The liquid can comprise an aqueous carrier, nonaqueous carrier, organic carrier or a combination thereof. The aqueous carrier can be water or an aqueous buffer, or combinations of water with one or more alcohols. The nonaqueous carrier can be an organic solvent, low molecular weight polymer, oil, silicone, other suitable material, alcohol, ethanol, methanol, propanol, isopropanol, poly(ethylene glycol), glycol, other such materials or a combination thereof. The terms liquid, binding liquid, printing fluid, binding fluid, and liquid may be used interchangeably to refer to a liquid delivered as part of 3DP.

In some embodiments, the equipment assembly comprises one or more, two or more, three or more, four or more or plural liquid reservoirs. The liquid can be colored or non-colored. The liquid can comprise pigment, paint, dye, tint, ink or a combination thereof. The liquid can comprise one or more solutes dissolved therein. The powder and/or liquid can comprise one or more binders. In one embodiment, the binding liquid can also include a binding agent. In some embodiments, the liquid may comprise an active ingredient.

In some embodiments, the binding liquid can be deposited on the upper surface of the powder layer in a pattern or over the entire surface. In some embodiments, the pattern of has a shape selected from the group consisting of an annular ring, a circle, a polygon, or any other desired shape. In some embodiments, the concentration (mass per unit area) of binding liquid applied to the upper surface of the powder layer in the pattern is uniform, while in other embodiments, a concentration of binding liquid applied in one or more portions of the pattern is more or less than a concentration of binding liquid applied in other portions. In some embodiments, wherein the layer of powder has a variance in thickness across the surface area, a higher concentration of binding liquid can be applied on a portion of the powder layer with a positive variance in thickness (thicker than the weight average thickness), and a lower concentration of binding liquid can be applied on a portion of the powder layer with a negative variance in thickness (thinner than the weight average thickness). Any one of the embodiments of this paragraph can be combined with any other embodiment described herein.

Non-limiting examples of powder materials and binding liquids are described in U.S. Pat. Nos. 9,339,489, 9,492,380, and 9,314,429, the disclosure of which is incorporated herein by reference. Any embodiment described herein can employ a binding liquid comprising water (which can include distilled and/or deionized water), an alcohol that can be selected from any lower linear or branched alcohol having from 1 to 3 carbon atoms, a soluble binder agent, an antioxidant, glycerin, and a surfactant or emulsifier. The printing fluid can comprise 1-25% weight, 5-20% weight, or 10-15% weight of at least one organic solvent, suitably an alcohol. A suitable alcohol can include ethanol, methanol, n-propanol, and isopropanol, or a combination thereof.

In some embodiments, the content of glycerin in the binding liquid ranges from at least about 0.1% by eight, up to about 20% by weight, including at least 0.5%, at least 1.0% and at least 1.5%, and up to about 10%, including up to about 5%, by weight. In some embodiments, the content of glycerin in the dosage form, based upon the final weight of the dosage form, ranges from at least about 0.05% by weight, including at least 0.1%, and at least 0.5%, and up to about 5%, including up to about 3%, up to about 2%, and up to about 1.0%, by weight.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims, and any amendments to the claims that incorporate any elements or features of embodiments described herein are recognized by persons skilled in the art as being directly and unambiguously derived from the description herein, as of the date of filing. All of the embodiments disclosed and claimed herein can be made and executed without undue experimentation in light of the present disclosure.

We claim:

1. A method of forming a dosage form within a portion of a packaging for the dosage form, comprising the steps of:
   1) providing a portion of a packaging for the dosage form, the portion of the packaging comprising at least one depression, the depression comprising a sidewall,
   2) depositing a predetermined first amount of a powder material comprising particles into a substantially uniform first powder layer within the at least one depression, wherein the sidewall has a depression depth, and the substantially uniform first powder layer has a thickness of at least 5%, and up to 50%, of the depression depth,
   3) depositing a binding liquid in a pattern on the first powder layer within the at least one depression, to bind at least a portion of the particles of the first powder layer to form an incremental first wetted powder layer,
   4) depositing a predetermined second amount of a powder material comprising particles into a substantially uniform second powder layer within the at least one depression and onto the first wetted powder layer, wherein the substantially uniform second powder layer has a thickness of at least 5%, and up to 50%, of the depression depth,
   5) depositing a binding liquid in a pattern on the second powder layer within the at least one depression, to bind at least a portion of the particles of the second powder layer to form an incremental second wetted powder layer, and
   6) optionally repeating steps 4) and 5) in sequence at least one or more times, thereby forming the dosage form within the portion of the packaging for the dosage form.

2. The method according to claim 1, wherein the at least one depression has a fixed shape and volume.

3. The method according to claim 1, wherein the packaging comprises a sheet including a plurality of the depressions formed into the sheet, and where the sidewall in the depression extends from the sheet to a closed end.

4. The method according to claim 1, wherein step 4) is repeated at least three times.

5. The method according to claim 1, wherein the powder material comprises particles of a binder material, and the binding liquid binds the particles of the binder material.

6. The method according to claim 1, further including a step, preceding step 2), of depositing an amount of a binding liquid on at least the closed end of the depression.

7. The method according to claim 1, wherein the at least one depression includes an inner surface that includes a release agent.

8. The method according to claim 1, wherein the binding liquid comprises a volatile solvent.

9. The method according to claim 8, further including a step of evaporatively removing, after step 3), a portion of the volatile solvent from the incremental first wetted powder layer, to form an incremental first bound powder layer.

10. The method according to claim 8, further including a step of evaporatively removing, after step 5), a portion of the volatile solvent from the incremental second wetted powder layer.

11. The method according to claim 1, wherein the pattern of the deposited binding liquid includes a peripheral pattern of binding liquid, applied to the powder layer at the inner surface of the depression.

12. The method according to claim 1, further including a step of applying a lidding layer over the dosage form and the at least one depression to form a sealed packaging for the dosage form.

13. The method according to claim 1, wherein the binding liquid is deposited by inkjet printing to form the dosage form.

14. The method according to claim 1, wherein the step 2) of depositing the predetermined amount of the powder material comprising particles into the substantially uniform powder layer within the at least one depression, comprises:
   1) depositing a predetermined amount of a powder material comprising particles into the at least one depression, and
   2) forming the deposited, predetermined amount of the powder material into a substantially uniform powder layer within the at least one depression.

15. The method according to claim 1, wherein the step of forming includes tamping a last deposited, predetermined amount of the powder material into a last formed powder layer having an upper surface.

16. A package comprising a film material having one or more depressions therein, the one or more depressions containing a shaped, bound-powder dosage form, formed within the one or more depressions according to the method of claim 1, and a peelable or removable covering sheet adhered to the film material, so as to enclose the bound-powder article within the one or more depressions.

17. The package according to claim 16, wherein a peripheral portion of the bound-powder article that confronts the inner surface of the one or more depressions includes an additional amount of a binding liquid.

18. The package according to claim 16, wherein the bound-powder article comprises a 3D printed, rapidly-dispersible dosage form.

19. The package according to claim 16, wherein the bound-powder article is formed within the one or more depressions by binding a powder deposited within the one or more depressions with a binding liquid.

20. The package according to claim 16, wherein the bound-powder article contains an active pharmaceutical ingredient (API).

\* \* \* \* \*

UNITED STATES PATENT AND TRADEMARK OFFICE
CERTIFICATE OF CORRECTION

| | |
|---|---|
| PATENT NO. | : 11,278,501 B2 |
| APPLICATION NO. | : 17/285186 |
| DATED | : March 22, 2022 |
| INVENTOR(S) | : Lauren E. Beach-Herrera et al. |

It is certified that error appears in the above-identified patent and that said Letters Patent is hereby corrected as shown below:

In the Claims

Claim 9, Column 36, Line 35, delete "powder laver" and insert --powder layer--.

Signed and Sealed this
Thirty-first Day of May, 2022

*Katherine Kelly Vidal*

Katherine Kelly Vidal
*Director of the United States Patent and Trademark Office*